(12) United States Patent
Chudzik

(10) Patent No.: US 8,242,179 B2
(45) Date of Patent: Aug. 14, 2012

(54) HYDROGEL-BASED JOINT REPAIR SYSTEM AND METHOD

(75) Inventor: Stephen J. Chudzik, St. Paul, MN (US)

(73) Assignee: Surmodics, Inc., Eden Prairie, MN (US)

( * ) Notice: Subject to any disclaimer, the term of this patent is extended or adjusted under 35 U.S.C. 154(b) by 1238 days.

(21) Appl. No.: 11/821,466

(22) Filed: Jun. 22, 2007

(65) Prior Publication Data

US 2008/0021563 A1    Jan. 24, 2008

Related U.S. Application Data

(60) Provisional application No. 60/816,131, filed on Jun. 23, 2006, provisional application No. 60/925,275, filed on Apr. 19, 2007.

(51) Int. Cl.
*A61K 47/34* (2006.01)

(52) U.S. Cl. .............. 514/772.7; 514/772.3; 514/777; 525/54.1; 525/54.2; 525/403

(58) Field of Classification Search .......... 525/54.1, 525/54.2, 403; 514/772.3, 772.7, 777
See application file for complete search history.

(56) References Cited

U.S. PATENT DOCUMENTS

| | | | |
|---|---|---|---|
| 5,410,016 A | 4/1995 | Hubbell et al. | |
| 5,562,736 A | 10/1996 | Ray et al. | |
| 5,672,662 A | 9/1997 | Harris et al. | |
| 5,739,208 A | 4/1998 | Harris | |
| 5,824,093 A | 10/1998 | Ray et al. | |
| 6,187,048 B1 | 2/2001 | Milner et al. | |
| 6,443,988 B2 | 9/2002 | Felt et al. | |
| 6,520,967 B1 | 2/2003 | Cauthen | |
| 6,676,971 B2 | 1/2004 | Goupil et al. | |
| 7,008,635 B1 | 3/2006 | Coury et al. | |
| 2005/0065616 A1 | 3/2005 | Ankorina-Stark et al. | |
| 2006/0093648 A1 | 5/2006 | Coury et al. | |
| 2008/0039931 A1 * | 2/2008 | Jelle et al. | 623/1.18 |

FOREIGN PATENT DOCUMENTS

| | | |
|---|---|---|
| WO | 92/10982 | 7/1992 |
| WO | 03/002021 A2 | 1/2003 |
| WO | 2004/047690 A2 | 6/2004 |

OTHER PUBLICATIONS

Bentley, M.D.; Roberts, M.J.; Harris, J.M.; Journal of Pharmaceutical Sciences, vol. 87(11), 1998, p. 1446-1449.*
Bulpitt, P.; Aeschlimann, D.; Journal of Biomedical Materials Research, 1999, p. 152-169.*
Park, Y.D.; Tirelli, N.; Hubbell, J.A.; Biomaterials, 2003, p. 893-900.*
PCT International Search Report for International Application No. PCT/US2007/014582, mailed on May 27, 2009.
Anseth et al. (1996) *Mechanical properties of hydrogels and their experimental determination*, Biomaterials, 17:1647-1657.
Patel et al. (2005) *Rheological and recovery properties of poly(ethylene glycol) diacrylate hydorgels and human adipose tissue*, Journal of Biomedical Materials, 73A:313-319.

* cited by examiner

*Primary Examiner* — James J Seidleck
*Assistant Examiner* — Robert Jones, Jr.
(74) *Attorney, Agent, or Firm* — Kagan Binder, PLLC

(57) ABSTRACT

The invention provides a system and method for treating an orthopedic condition using a hydrogel-forming composition, which forms a hydrogel in situ at a target location and at least bio-mechanically treats the condition. The invention also provides a hydrogel forming composition designed to form a hydrogel with desirable biocompatible and biomechanical properties. In some aspects the hydrogel is formed in a water-permeable casing, which is delivered to an orthopedic joint in a minimally invasive manner. In particular, the system and method can be used for intervertebral disc replacement or repair.

14 Claims, 6 Drawing Sheets

HYDROGEL-BASED JOINT REPAIR SYSTEM AND METHOD

CROSS-REFERENCE TO RELATED APPLICATIONS

The present non-provisional patent application claims priority under 35 USC §119(e) from U.S. Provisional Patent Application having Ser. No. 60/816,131, filed on Jun. 23, 2006, and titled HYDROGEL-BASED JOINT REPAIR SYSTEM AND METHOD; and U.S. Provisional Patent Application having Ser. No. 60/925,275, filed on Apr. 19, 2007, and titled BIODEGRADABLE MATRIX MATERIALS; wherein the entirety of said provisional patent applications are incorporated herein by reference.

FIELD OF THE INVENTION

The invention relates to systems and methods for the treatment of medical conditions associated with joints. The invention is directed to a hydrogel-forming composition, and a system including the composition and a casing for containing the hydrogel. The system can be used in a minimally invasive method for treating a joint.

BACKGROUND OF THE INVENTION

Movement within the musculoskeletal system is dependent upon functional joints. Significant pain can be associated with dysfunction joints and can present an individual with physical limitations. Pain caused by problems associated with the spine is a common ailment in adults and affects millions of individuals each year in the United States. The management of chronic back pain remains challenging even in view of currently available operative and non-operative techniques.

Various surgical procedures are used on patients having chronic back pain. These include (a) intradiscal procedures, which can include injections (epidurals), electrothermal exposure, and nerve stimulation; (b) fusion of the spine (arthrodesis); and (c) intervertebral disc excision (discectomy).

Medical procedures involving spine fusion have been practiced for many decades. However, these techniques remain controversial and the results remain unclear.

Intervertebral disc replacement is an attractive alternative to spine fusion. Disc replacement offers the advantages of restoration of segmental mobility in the spine, elimination of pain, and improvement in the distribution of biomechanical forces in the spine.

Approaches to restoration of the function of a degenerated or dysfunctional disc include biological reconstruction and artificial disc replacement. Prosthetic devices that can be used for the replacement of the intervertebral discs can be divided into two general categories. One category is devices that replace the nucleus only, leaving the annulus and cartilaginous portions of the endplate intact. A second category is devices that replace the entire intervertebral disc.

While artificial disc replacement is viewed as a distinct improvement over techniques such as spine fusion, many replacement processes are particularly invasive. Commonly performed replacement processes entail insertion of relatively large artificial discs. These invasive procedures can involve the significant resection of tissue in order to gain access to the injury site. This may increase the risk of complications, such as infection and spine trauma associated with the insertion of the disc. Furthermore, these procedures may require extensive hospitalization and therapy following the procedure. Given this, these more invasive procedures are only used in more serious cases of spine problems.

In addition to issues of invasiveness, many disc replacement techniques involve the use of biomaterials that are not ideally suited as replacement materials for a normal intervertebral disc. A normal intervertebral disc includes a nucleus, composed primarily of proteoglycans and Type II collagen with a capacity to absorb and distribute load, and an outer annulus with well-organized layer of Type I collagen that serve to stabilize the motion segment. The composition and arrangement of these natural tissues in a healthy intervertebral disc provide unique biomechanical properties. Currently available systems are not able to sufficiently mimic these properties of a normal intervertebral disc.

SUMMARY OF THE INVENTION

The present invention provides methods and systems for treating problems associated with orthopedic joints within the body.

In some aspects, the invention provides an artificial article (herein referred to as a "pillow") intended for use within an orthopedic joint. The pillow provides cushioning and improves function of the joint. The invention also provides minimally invasive methods for forming the pillow within the joint.

In one aspect, the invention provides a system for forming a pillow within an orthopedic joint. The system comprises a water-permeable casing configured for insertion into the joint space, and a composition comprising a hydrogel-forming material. The system is minimally invasive since both the casing and the hydrogel-forming material are delivered to the joint space with nominal tissue disruption. That is, the casing is delivered to a target location within a joint in a compact configuration, and then the hydrogel-forming material is delivered within the casing via one or more conduits. The casing is filled with the hydrogel-forming material in situ, and the hydrogel if formed into a desired shape.

In specific aspects, the system includes a casing that is configured for insertion into an intervertebral space. In particular, the pillow can be formed within the intervertebral space to replace the function of all or a portion of a normal intervertebral disc. The intervertebral pillow of the present invention has improved biomaterial properties and is thought to more closely mimic the function of a normal intervertebral disc as compared to currently available technologies.

In one particular aspect, the present invention provides a method for insertion of a pillow within the intervertebral space. The method comprises the steps of providing a water-permeable casing in a compact configuration; delivering the casing to an intervertebral space; and then filling the casing with a composition comprising a hydrogel-forming material. In the step of delivering or filling (or both steps) the casing becomes "uncompacted," and essentially spreads out in the intervertebral space. During or after the step of filling, the composition forms a hydrogel within the casing to provide the intervertebral pillow.

Further, and in other aspects, the casing can be delivered to the intervertebral space in an arthroscopic procedure using an insertion instrument. For example, in the step of providing, the casing can be loaded into the lumen of a distal end of an insertion instrument. In the step of delivering the casing can be deployed from the distal end of the instrument into the intervertebral space.

The water-permeable casing is relatively thin. In some aspects the casing has a thickness in the range of about 0.1 mm to about 0.5 mm. The relative thinness of the casing allows it to be significantly compacted, facilitating the minimally invasive method. In some aspects, the casing is in a compacted configuration of a scroll or volute. This allows the casing in the compacted configuration to have a cross-sectional diameter of about less about 1 cm, or less than about 0.5 cm. One desirable cross sectional diameter is in the range of about 0.2 to 0.5 cm. Following deployment to a target location within the joint, the casing can unroll from the scroll or volute configuration.

The casing can also provide structural support to the hydrogel formed in situ. In this regard, the casing not only serves as a mold to promote shaping of the hydrogel-forming material within the joint, but also supplements the strength of the hydrogel.

One advantage of the present invention relates to the ability to form a pillow that occupies a significant volume of the intervertebral space in a minimally invasive manner. For example, the present methods do not require the placement of multiple, smaller pillows in the intervertebral space to provide adequate cushioning to the vertebral column.

In addition, the inventive methods reduce the likelihood of complications otherwise associated with insertion of joint prosthesis, such as artificial discs. For example, the present methods can reduce the risk of infection and spine trauma associated with invasive surgical techniques involving the spine. The present techniques can also result in less pain, scarring, and recovery time for the patient.

In addition to the advantages that the present inventive method and system offer with regard to invasiveness, the system is also designed to provide improved function following implantation. In particular, the system that includes the hydrogel can provide desirable bio-responsive features. In some aspects, following its formation, the pillow closely mimics the function of a natural intervertebral disc. The desirable features are at least in part afforded by the physical properties of the hydrogel formed within the casing of the pillow. For example, the hydrogel has a tensile modulus and gel strength that provides adequate support and cushioning when pressure is exerted on the vertebral column. In addition, the hydrogel is substantially hydrophilic and capable of absorbing water when in use. Following relief of compressive forces within the spine, the hydrogel is capable of rehydrating. For example, when pressure is relieved from the vertebral column (such as when the person is in a supine or prone position) the synthetic intervertebral pillow can expand to a limited extent. The expansion is caused by rehydration of the hydrogel. These desirable properties can be provided by a hydrogel-forming composition that includes macromer components, as described herein.

In another aspect of the invention, it has been discovered that combinations of selected polymer-based hydrogel-forming components are particularly useful in systems for the treatment of an orthopedic joint.

The system includes at least two polymer components, one polymer providing strength to the hydrogel, and the other providing significant water retention properties to the hydrogel. Therefore, in this aspect, the invention provides a hydrogel forming system useful the treatment of an orthopedic condition, comprising a first polymer having a molecular weight of less than 5000 Da, and second polymer that is hydrophilic. The second polymer can be derived from a polysaccharide or polypeptide. The second polymer can be highly hydrophilic and comprise a plurality of pendent charged groups. In some aspects, the first polymer has a molecular weight of less than 5000 Da and is a poly(alkoxyalkane), and the second polymer comprises a polysaccharide. In some aspects, the first polymer has a molecular weight of less than 2500 Da, and the second polymer comprises pendent carboxylate groups. The first and second polymers can include pendent coupling groups that can be reacted to form a crosslinked hydrogel matrix.

DETAILED DESCRIPTION

Figure 1:
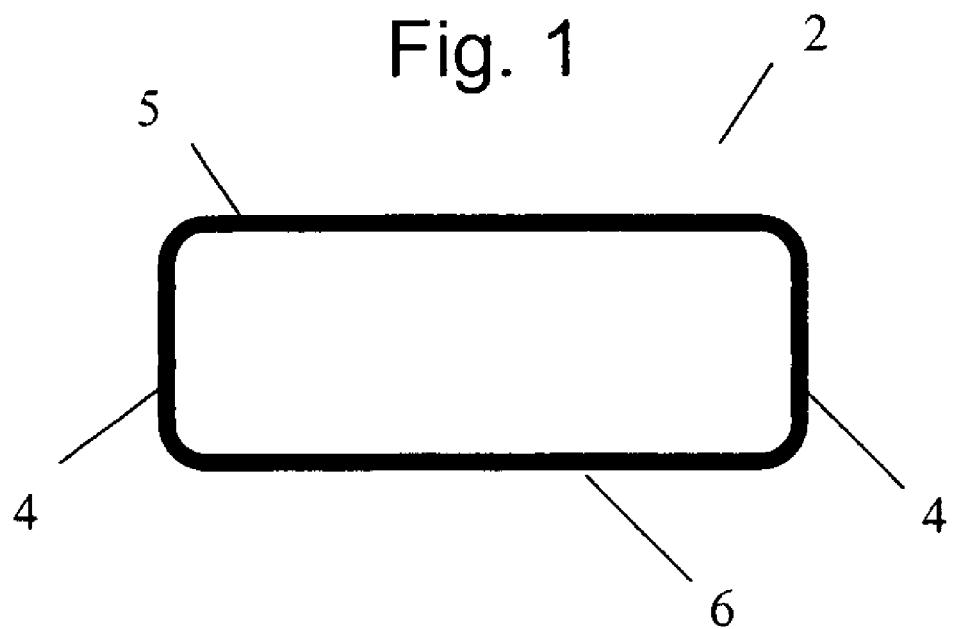
FIG. 1 is an illustration of a cross section of an intervertebral pillow.

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The system and method of the invention can be used in any joint where cushioning is desired. For example, a pillow of the present invention can be formed in joints having one or more articulations, such as amphiarthroidal, synarthroidal, or diarthroidal joints.

The system and method of the invention can be used for the treatment of osteoarthritis, a degenerative joint disease. Treatment can be carried out in localized areas of the body such as arthritic joints of the knee, hip, hands, feet, shoulder, and spine.

The system of the invention can be used to treat a condition where an orthopedic abnormality results in nerve pain. For example, the hydrogel composition can be used to relieve pressure on a pinched nerve, which may be manifested in a neuroma, or a scarring of the nerve. For example, the hydrogel-forming composition can be used to treat Morton's neuroma, which is characterized by a thickening of the tissue around one of the digital nerves of the foot.

While the system and methods are applicable to any joint, the invention is exemplified by discussion of features of the present invention in relation to the treatment of joints within the vertebral column, in particular, intervertebral joints.

The system of the present invention can be used repair or replace a portion of the joint. For example, in some aspects, system of the invention can be used to replace or enhance the function or the structure of the natural tissue of the joint. The natural tissue of the joint that is displaced by the hydrogel of the invention can include various cartilage types, such as fibrocartilage or hyaline cartilage.

In one aspect, the invention provides a system that includes a casing configured for use within an orthopedic joint, and a hydrogel-forming composition that can be delivered within the casing to form a hydrogel. The casing of the present invention is designed to be deployed in a joint and is constructed so that all or a portion of the joint will be occupied by the pillow. The pillow is formed by filling the casing with the hydrogel-forming material. The shape of the pillow can be affected by the construction of the casing, the shape of the joint, or a combination of the two. In some aspects, the casing can be constructed in a manner so that when it is filled with the hydrogel-forming material, it molds the material into a particular shape.

In exemplary embodiments, the casing is constructed to provide a shape, that when filled with the hydrogel material, forms a pillow that occupies all or a portion of the intervertebral space. The intervertebral space is normally (i.e., in a healthy individual) occupied by the intervertebral disc, which consists of the annulus, which is a robust collagenous tissue that encompasses the nucleus pulposus, which is a softer gel-like tissue. The annulus, is composed primarily of elastic collagen fibers, proteoglycans, and water, and functions to resist compressive vertebral forces and enhances the spine's rotational stability. The nucleus also includes collagen and proteoglycans, but has a higher water content than the annulus. The nucleus also functions to resist compressive vertebral forces.

The casing can be constructed to occupy a portion of the intervertebral space when deployed in the intervertebral space and filled with the hydrogel composition (i.e., in the pillow configuration). For example, the portion of the intervertebral space occupied by the pillow can be the portion that is normally occupied by the nucleus. In some cases the portion can be all of the intervertebral space (the space normally occupied by the nucleus or the annulus). In one desirable construction, the casing is made so that it occupies a significant volume in the intervertebral space. For example, the casing can be configured and conform to the area of the intervertebral disc that normally includes the nucleus.

The construction and dimensions of the casing can provide an overall shape to the pillow. In many cases, the casing construction will provide a pillow having a height in the range from about 5 mm to about 15 mm. In many cases, the pillow can have a width and length in the range of about 10 mm to about 30 mm. The pillow, when filled with the hydrogel, will have a height, width, and length. In some aspects, the pillow can occupy a volume of about 750 mm$^3$ or greater.

FIG. 1 shows a cross section of a pillow 2 having a generally rectangular cross-sectional shape. The casing of the pillow can have sidewalls 4, which, in some aspects, are in contact with the annulus. The top 5 and bottom 6 surfaces of the casing can be in contact with the faces of the vertebra.

The volume that the pillow occupies in the intervertebral space can vary somewhat depending on certain factors, such as the hydration state of the hydrogel within the pillow and the expansion properties of the pillow, including the elasticity of the casing and the swellability of the hydrogel. However, in desired aspects the hydrogel has limited swellability and does not experience significant expansion or contraction within the joint. In some cases the volume of the pillow can fluctuate up to about 10% in the joint during use. In some constructions, when in use, the pillow occupies a volume of in the range of about 750 mm$^3$ to about 5000 mm$^3$.

The casing is water-permeable and allows fluid to flow in and out of the pillow in the joint. The water-permeable casing is relatively thin, and can have a nominal thickness in the range of about 0.1 mm to about 0.5 mm. This thickness allows the casing to be compacted for insertion into the joint in a minimally invasive manner. Because the casing can be folded into a compact configuration for insertion into a patient, the casing is generally malleable.

Generally, the casing can be constructed from any suitable biomaterial, or combination of biomaterials, that allow for water permeability. The casing can be formed from a fabric made of synthetic and/or natural polymeric materials. Exemplary synthetic polymeric materials that can be included in the casing include polyesters, such as Dacron™ or PET (Polyethylene terephthalate), or polytetrafluoroethylene (PTFE), such as Teflon™.

The casing can also include a plurality of apertures, such as microapertures, that also allow the flux of body fluids. These apertures can be large enough to allow the flux of body fluids in and out of the pillow. However, the apertures are small enough to prevent substantial leakage of the hydrogel-forming material out of the casing when it is provided to the interior of the casing.

The casing can be prepared by joining fabric pieces by stitching, adhesive, or heat treatment. In a simple construction, the casing can be prepared by folding a piece of fabric upon itself, and then joining the edges of the fabric, for example by stitching, etc. In another construction two pieces of fabric are joined at the edges. In yet other constructions more than two pieces of fabric are joined at their edges to produce the casing.

The fabric can also have a degree of stretchability. A casing formed from stretchable fabric can be useful in various aspects of the invention. In procedures where the casing is deployed within the intervertebral space with at least a partially intact annulus, the stretchable casing can be filled with the hydrogel-forming material and expand and stretch to contact the walls of the adjacent vertebra and the annulus.

Following implantation, the stretchable property can allow the pillow to expand and contract upon movement of fluids in and out of the pillow. In some aspects, as based on the desirable properties of the hydrogel, such expansion and contraction may be limited. The stretchable property can accommodate the increase in volume in the hydrogel when in a maximally hydrated state and will prevent rupturing of the casing, or loss of the hydrogel through the casing due to hydrogel material pressure. However, the stretchable casing can still offer a degree of support to the hydrogel structure. In some cases the material has a degree of stretchability up to about 10%.

In some aspects the casing is resilient. That is, the casing has properties that promote its transition from a compacted configuration to an uncompacted configuration. To illustrate this property in the context of the present invention, the insertion of a casing with a resilient property in a target location in a joint is described. For example, the casing with a resilient property can be compacted (such as by folding or rolling) and held in the compacted configuration by a portion of an insertion instrument. When the casing is deployed from the instrument into the target site, it has a tendency to assume the shape of the pillow because of the resilient property.

In order to provide a resilient property, a particular casing material can be used, or the casing can be treated to provide a degree of resiliency. One way of providing a resilient casing is to prepare a casing having at least two different portions. A first portion of the casing has a different physical or chemical property or properties than a second portion of the casing. For example, the casing may be formed from two different fabrics that are joined together to form the casing. The fabric forming the first portion can be thicker than the other fabric. The thicker fabric can cause the casing to be resilient and have a tendency to unfold or unroll from a compacted state to an uncompacted state.

Alternatively, one portion of the casing can have a property that is different than another portion (other than a different dimension). For example, the first portion can be treated with an agent to change its physical characteristics (such as stiffness).

Alternatively, the first portion is formed from a fabric that is a different fabric type from the fabric of the second portion.

The casing can also be treated with a stiffening agent to provide a resilient casing. In doing so, a casing can be expanded to the shape of the pillow that is to be formed in the intervertebral space and then the stiffening agent can be applied to the casing. For example, the casing may be expanded by filling with an inert material or expanding a balloon within the casing. In the expanded form, the casing can be treated with a stiffening agent, such as cellulose. The stiffening agent will generally not block the ability of the casing to flux fluid when in use in the body. After the casing has been treated, the inert material can be removed and the casing can be collapsed. The casing can then be formed into the compacted shape and placed within the distal end of the insertion instrument. Upon deployment from the distal end of the instrument, the resilient properties of the casing predisposes the casing to transform from the compacted shape to an uncompacted shape (e.g., the shape of the pillow) within the target space.

In the method and system of the present invention, the casing can be compacted so that it can be delivered to the joint space in a minimally invasive manner. For example, the casing can be in a compacted form of a scroll or volute, which allows it to pass through an incision or other opening during delivery to a target location within an orthopedic joint. The casing in the compacted form can be flexible, which may allow flexion during the insertion process. In some aspects, the casing is compacted to have a cross-sectional diameter of about less about 1 cm, and more specifically less than 0.5 cm. In one aspect the cross sectional diameter is in the range of about 0.2 cm to about 0.5 cm.

Figure 2:
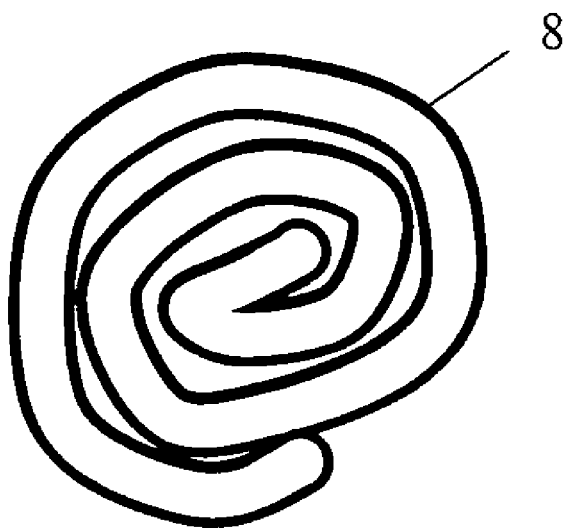
FIG. 2 is an illustration of a cross section of a casing in a scrolled compact configuration.

Various compact configurations of the casing are contemplated. In some aspects the compact configuration comprises a cross sectional shape that is rounded or circular. For example, the casing 8 is formed into a scroll or volute, as exemplified by the configuration shown in FIG. 2. Upon delivery of the casing in a scrolled or volute compact configuration, the casing can be unrolled or unfurled to spread out the casing in the portion of the intervertebral space.

In another aspect, the casing in the compact configuration is folded. A casing that is folded may have a cross sectional shape of a square or rectangle. The casing in the compact configuration may include a plurality of folds (pleats). When the casing transitions from a compact to an uncompact configuration in the joint, the casing can expand in a manner similar to that of an expanding accordion.

The casing can also include one or more agents that promote formation of the hydrogel following delivery of the hydrogel-forming material within the casing. For example, the casing can be associated with a polymerization initiator, which can contact and promote formation of a hydrogel from a polymerizable hydrogel-forming material. The polymerization initiator is desirably located in the inner portion of the casing so that upon filling of the casing, the hydrogel-forming material comes into contact with the initiator to commence hydrogel formation. Prior to delivering the casing to the joint, the polymerization initiator can be sprayed or soaked on the casing material, such as fabric.

The polymerization initiator can be a co-initiator, such as a member of a redox pair, such as a reducing agent or an oxidizing agent. The other member of the redox pair can be present in the composition that includes the hydrogel-forming material.

In another aspect, the hydrogel-forming composition can be delivered directly into a joint without a casing. The hydrogel-forming composition can set up within the joint to form a hydrogel that directly treats the joint. In some modes of practice, the hydrogel-forming composition is injected into a joint using a cannula or needle. The composition can be prepared to cure quickly upon injection so that the hydrogel-forming material does not diffuse out of the area of injection.

Various materials can be used to form the hydrogel of the present invention. A hydrogel forming composition can be prepared to have desirable physical properties for use in the present system. For example, the formed hydrogel can be biocompatible, have relatively low swellability, have a relatively high tensile modulus, and be substantially or completely non-biodegradable. In exemplary preparations the hydrogel has properties of sufficient firmness (tensile modulus) to provide cushioning similar to that of a natural intervertebral disc. The hydrogel also is highly hydrophilic and can readily absorb water; however, the hydrogel has limited swellability and does not experience considerable volumetric expansion upon hydration.

The hydrogel-forming material is used in a hydrogel-forming system that promotes its transition from a flowable form to a hydrogel form. For example, the flowable form of the hydrogel composition is capable of being delivered to an interior portion of the pillow in situ, or directly into a joint. The hydrogel can be formed by any type of process, or combinations of processes, such as a physical process, chemical reaction, and/or mechanical process. The process essentially promotes the conversion of the flowable form of the composition to the hydrogel form. The system can include any one or more suitable curing agent(s), including commercially available curing agents that initiate and/or promote the formation of the hydrogel. The curing agents can promote formation of the hydrogel by an external stimulus, such as by heat or radiation, or by the action of combining the curing agents.

In the hydrogel-forming process, the period of time between the initiation of hydrogel formation, and point that the hydrogel achieves its cured form is referred to as the hydrogel-forming period. This hydrogel-forming period can be controlled by one or more factors, such as the type and amount of hydrogel forming materials used in the composition, and the type and amount of reagent(s) that are used to initiate and propagate hydrogel formation. In many aspects, the hydrogel-forming period is longer than the amount of time it takes to deliver the hydrogel-forming composition to the casing. In some modes of practice, the gel forming period is about 30 seconds or greater, or about from 30 seconds to about 5 min.

A hydrogel having properties that are desirable for use within a joint can be prepared using one or more approaches based on the chemical characteristics of the components used to form the hydrogel. For example, the hydrogel can be formed having a high degree of crosslinking. This can limit the swellability of the hydrogel and increase its tensile modulus. Another approach is to use hydrogel-forming material that is partially hydrophobic in order to increase the hydrophobicity of the hydrogel. This can effectively repel water and limit the swellability of the formed hydrogel. Yet another strategy is to use lower molecular weight components that increase the solids content and therefore the density of the hydrogel.

The composition that includes hydrogel-forming materials can include one or more components that can be reacted to form a hydrogel within the casing. In many cases, polymeric material is used to form the hydrogel. The hydrogel can be formed using coupling groups that allow polymers to be crosslinked, wherein the crosslinks include covalent bonds. A "coupling group" can include (1) a chemical group that is able to form a reactive species that can react with the same or similar chemical group to form a bond that is able to couple polymers together (for example, wherein the formation of a reactive species can be promoted by an initiator); or (2) a pair of two different chemical groups that are able to specifically react to form a bond that is able to couple polymers together. Coupling groups can be attached to any one or more polymers used to form the hydrogel.

Contemplated reactive pairs include Reactive Group A and corresponding Reactive Group B as shown in the Table 1 below. For the preparation of a composition that forms a hydrogel, a reactive group from group A can be selected and pendent from a first set of polymers and a corresponding reactive group B can be selected and pendent from a second set of polymers. Reactive groups A and B can represent first and second coupling groups, respectively. At least one and generally two, or more than two reactive groups are pendent from an individual polymer. The first and second sets of polymers can be combined and reacted, for example, thermochemically, if necessary, to promote the coupling of polymers and the formation of the hydrogel.

TABLE 1

| Reactive group A | Reactive group B |
|---|---|
| amine, hydroxyl, sulfhydryl | N-oxysuccinimide ("NOS") |
| amine | Aldehyde |
| amine | Isothiocyanate |
| amine, sulfhydryl | Bromoacetyl |
| amine, sulfhydryl | Chloroacetyl |
| amine, sulfhydryl | Iodoacetyl |
| amine, hydroxyl | Anhydride |
| amine, hydroxyl | Imidazole carbonate |
| aldehyde | Hydrazide |
| amine, hydroxyl, carboxylic acid | Isocyanate |
| amine, sulfhydryl | Maleimide |
| sulfhydryl | Vinylsulfone |

Amine also includes hydrazide (R—NH—NH$_2$)

For example, a suitable coupling pair would be a hydrophilic polymer having an electrophilic group and a hydrophilic polymer having a nucleophilic group. An example of a suitable electrophilic-nucleophilic pair is N-hydroxysuccinimide-amine pair, respectively. Another suitable pair would be an oxirane-amine pair.

Accordingly, in some modes of preparation, the hydrogel can be formed by at least a hydrophilic polymer having two or more first reactive groups (described herein as the "A component"), and a hydrophilic component that includes two or more second reactive groups (described herein as the "B component"). Upon mixing, the first and second groups specifically react, coupling the hydrophilic polymer to the hydrophilic component and forming a hydrogel.

Various A-B combinations can be used. In some cases, the B component is the same as the A component, with the exception that the second reactive group is different than the first reactive group. The hydrogel can be formed predominantly or entirely of the A and B components.

In one preparation, the A component is a hydrophilic polymer comprising reactive amine groups. The reactive amine groups may be present on the polymer naturally, e.g., chitosan, or amines can be added to the polymer using standard chemistries involving activation of hydroxyl or carboxyl groups followed by reaction with a diamine.

In some cases a natural polysaccharide, such as maltodextrin, polyalditol, or amylose, is used to form the A component. To prepare the A component, and as an example, a portion of the hydroxyl groups of the natural polysaccharide are derivatized with first reactive groups that are amine groups to provide an aminated polysaccharide. Various reaction schemes known in the art can be used to provide a natural polysaccharide with pendent amine groups. In one mode of practice, the polysaccharide is subjected to a two-step reaction scheme to provide pendent amine-reactive groups. In a first step the polysaccharide is reacted with a hydroxyl reactive compound to provide a linking group, to which an amine-containing compound is reacted, providing amine groups that are pendent from the polysaccharide and which represent the first reactive group. In the first step, the hydroxyl-reactive compound is used at a concentration to provide a desired degree of substitution on the polysaccharide.

In some aspects, a non-reducing polysaccharide is used to form the A component. For example, the non-reducing polysaccharide is polyalditolo, which has a non-reducing terminus (e.g, the polysaccharide does not have an aldehyde group on its terminal end).

Non-reducing polysaccharides are advantageous when amine groups are introduced or present on either the A or B component, as they do not contain pendant aldehyde groups. Pendant aldehyde groups may react with the pendant amine groups on the amine-functional polysaccharide and cause a reduction in the reactivity and/or shelf-life of the amine-functional polysaccharide.

The reaction scheme described above may be varied in order to produce aminated polysaccharides having varying degrees of substitution (DS). As used herein the term "degree of substitution" generally refers to the number of hydroxyl groups, on average, per glycopyranose monomeric residue that are derivatized (a polysaccharide such as maltodextrin has three hydroxyl groups per monomeric residue; maltodextrin having a DS1 has approximately 1 hydroxyl group per monomeric residue substituted). In some embodiments, the degree of substitution (DS) of the polysaccharide ranges from about 0.1 to about 1.0. In more specific embodiments, the degree of substitution ranges from about 0.2 to about 0.3, although other degrees of substitution may be desirable. In an exemplary embodiment, polyalditol is reacted with CDI followed by 1,6-diaminohexane in order to produce an aminated polyalditol having a degree of substitution ranging from about 0.2 to about 0.3. The synthesis of aminated polyalditol is described herein.

In some aspects of the invention, the hydrogel is formed by the reaction of at least component A that comprises an aminated polysaccharide, and component B that comprises an amine-reactive hydrophilic compound.

As an example, and for use with an aminated polysaccharide, Component B can be any suitable hydrophilic biocompatible compound that has two or more amine-reactive groups (i.e., the second reactive groups).

In one mode of preparation, component B is a hydroxyl-containing compound that is chemically modified in order to introduce amine-reactive functional groups. Desirably, hydroxyl-containing compounds having at least two pendant hydroxy groups (typically 2 to 4), having biocompatibility, having appreciable water-solubility, and having a molecular weight of about 10,000 Da or less, or about 10,000 Da or less, are used for the synthesis of the B component.

In many embodiments, the hydroxyl groups are present as pendant groups from a hydrophilic compound having a hydrophilic organic backbone that comprises atoms of carbon, hydrogen, and oxygen. In some embodiments, the organic backbone is an alkoxyalkane backbone. Representative examples of hydrophilic compounds of this type include polyalkoxyalkane such as poly(ethylene glycol), tetraethylene glycol, triethylene glycol, trimethylolpropane ethoxylate, and pentaeerythritol etholxylate. In some aspects the hydrophilic compound is a liquid at about room temperature (~25° C.). In many embodiments, a particular hydroxyl-containing compound is an ethylene glycol polymer or oligomer having the structure $HO-(CH_2-CH_2-O)_n-H$. Typically, the value of n ranges from about 3 to about 150 and the number average molecular weight (Mn) of the poly(ethylene glycol) ranges from about 100 Da to about 5000 Da, more typically ranging from about 200 Da to about 3500 Da.

Various synthetic schemes can be used to provide the hydrophilic compound with amine reactive groups. In one mode of practice, the amine-reactive compound is formed by reacting the hydroxy functional compound with 1,1'-carbonyldiimidazole (CDI), which is described herein.

As another example of preparation of a B component having second reactive groups, an amine-reactive compound is prepared by first reacting succinic anhydride with a polyol (e.g., a diol, triol, or tetrol) to form a multi-functional carboxylic acid compound. The succinic anhydride reacts with the hydroxyl groups on the polyol to form an ester linkage and a terminal carboxylic acid group. The multifunctional carboxylic acid compound is then reacted with N-hydroxysuccimide (NHS) which reacts with the terminal carboxylic acid groups to form an amine-reactive NOS groups.

In view of the reactive nature of the first component and the second component, these components are typically held in separate containers from one another until prior to the time that formation of the hydrogel. When the formation of the hydrogel is desired, the A and B components are mixed with one another in the desired ratio to initiate formation of the hydrogel.

Typically, the A and B components are reacted with one another in a desired stoichiometric ratio in order to form the hydrogel. As one way of describing the amount of components A and B used to form the matrix, a particular stoichiometric ratio of the number of moles of amine groups in the amine-functional polysaccharide to the number of moles of amine-reactive groups in the amine-functional compound is used. For example, the stoichiometric ratio of amine groups to amine-reactive groups can be in the range from about 1:5 to about 5:1.

After initiating the formation of the matrix material by reacting the A component with the B component, the components typically cure to form the hydrogel in a time period that ranges from about tens of seconds to several minutes. More typically, the components cure to form the matrix material in a time period that ranges from about 1 minute to about 60 minutes.

One method of adjusting the rate of reaction is to control the pH of the composition that includes the mixture of the A and B components. Generally speaking, for chemistries using first and second groups that are amine and amine-reactive groups, a higher pH will favor a faster reaction rate, whereas a lower pH will favor a slower reaction rate between the first and second components. In most embodiments, the pH is controlled between a lower pH limit of about 7.5 and an upper pH limit of about 9.5, although other pH values may be suitable for certain applications. The pH of the hydrogel forming material may be controlled by buffering the first and/or second components using conventional buffering materials such as phosphate, borate, and bicarbonate buffers.

The cure time of the composition can also be adjusted by changing the molecular weight of the B component (e.g. the amine reactive component). Typically, amine reactive components formed from lower molecular weight polyol components (as compared to higher molecular weight polyol components) favor high reactivity (i.e., shorter cure times). This can be accomplished, for example, by controlling the molecular weight of the hydroxyl-functional material that is used to form in the amine-reactive component.

The molecular weight and functionality of the B component (e.g., amine-reactive component) can also affect the physical properties of the matrix formed upon cure. As such, the B component can be chosen to provide a hydrogel with particular physical properties. The present invention shows that B components having a lower molecular weight (such as lower molecular weight poly(ethylene glycols)) provide a matrix having an increase in one or more of density, and/or hardness. By contrast, as the molecular weight of the B component increases, the matrix material becomes softer and more flexible.

A similar observation can be made with respect to functionality. As the functionality of the B component increases, the matrix has an increase in one or more of density, and/or hardness.

In some modes of preparation, the hydrogel-forming composition comprises a macromer. Macromers include one or more "polymerizable group(s)" which generally refers to a chemical group that is polymerizable in the presence of free radicals. Polymerizable groups generally include a carbon-carbon double bond which can be an ethylenically unsaturated group or a vinyl group. Exemplary polymerizable groups include acrylate groups, methacrylate groups, ethacrylate groups, 2-phenyl acrylate groups, acrylamide groups, methacrylamide groups, itaconate groups, and styrene groups.

Polymers can be effectively derivatized in organic, polar, or anhydrous solvents, or solvent combinations to produce macromers. Generally, a solvent system is used that allows for polymer solubility and control over the derivatization with polymerizable groups. Polymerizable groups such as glycidyl acrylate can be added to polymers (including polysaccharides and polypeptides) in straightforward synthetic processes. In some aspects, the polymerizable group is present on the macromer at a molar ratio of 0.05 µmol or greater of polymerizable group (such as an acrylate group) per 1 mg of macromer. In some aspects the macromer is derivatized with polymerizable groups in amount in the range from about 0.05 µmol to about 2 µmol of polymerizable group (such as an acrylate group) per 1 mg of macromer.

For example, a natural polymer such as hyaluronic acid can be reacted with a compound containing a polymerizable group, such as glycidyl acrylate, in the presence of formamide (and TEA, for pH control) to provide acrylate-derivatized hyaluronic acid molecules. The number and/or density of acrylate groups can be controlled using the present method, e.g., by controlling the relative concentration of reactive moiety to saccharide group content.

Crosslinker chemistry can also be used to add polymerizable groups to a polymer. For example, polymers can be derivatized with varying amounts of vinyl containing compounds such as vinylbenzoic acid. Polymer preparations can be mixed in the cold followed by the addition of a crosslinker such as 1-ethyl-3-(3-dimethylaminopropyl) carbodiimide.

The macromer can be subject to purification, for example, by dialysis, before use in the matrix-forming composition.

In some aspects, the hydrogel-forming composition includes, as starting components, a higher molecular weight reactive polymer (macromers). Macromers generally include one or more reactive groups which allow them to become associated with each other following reaction of the reactive groups. In many cases macromers include polymerizable groups, such as ethylenically unsaturated groups Generally, macromers have a molecular weight of about 500 Da or greater. In some modes of practice, macromers are used as a primary component in the hydrogel-forming composition and have a molecular weight in the range of about 1000 Da to about $2 \times 10^6$ Da.

Any type of macromer can be included in the hydrogel-forming composition of the invention. The macromer can be based on a synthetic or a natural polymer. Generally, the macromer or macromers used are substantially or entirely non-biodegradable.

Exemplary macromers that can be used include synthetic macromers based on the following polymers: poly(vinylpyrrolidone) (PVP), poly(ethylene oxide) (PEO), poly(ethyloxazoline), poly(propylene oxide) (PPO), poly(meth)acrylamide (PAA) and poly(meth)acylic acid, poly(ethylene glycol) (PEG) (see, for example, U.S. Pat. Nos. 5,410,016, 5,626, 863, 5,252,714, 5,739,208 and 5,672,662) PEG-PPO (co-polymers of polyethylene glycol and polypropylene oxide), hydrophilic segmented urethanes (see, for example, U.S. Pat. Nos. 5,100,992 and 6,784,273), and polyvinyl alcohol (see, for example, U.S. Pat. Nos. 6,676,971 and 6,710,126).

One particular synthetic macromer has a molecular weight of about 5000 Da or less, and more specifically 2500 Da or less.

The hydrogel-forming composition can also include a macromer that is based on a natural polymer. Exemplary natural polymers include polysaccharides and polypeptides. Naturally occurring polysaccharides include polysaccharide and/or polysaccharide derivatives that are obtained from natural sources, including plants, animals, and microorganisms. The naturally occurring polysaccharide can be a homoglycan or a heteroglycan; exemplary heteroglycans include diheteroglycans and triheteroglycans. These naturally occurring polysaccharides can also be derivatized to provide pendent reactive groups that are members of a reactive pair, as described herein.

Desirably, the polysaccharide is highly hydrophilic and has the capacity of absorbing water when polymerized in the hydrogel in macromer form.

Exemplary naturally occurring polysaccharides include dextran, hyaluronic acid, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, and galactomannans.

In one aspect a hyaluronic acid macromer is included in the hydrogel-forming composition. Hyaluronic acid is a nonadhesive (to proteins), nonimmunogenic, and naturally derived linear polymer that includes alternating β1,4-glucuronic acid and β1,3-N-acetyl-D-glucosamine units. HA is the principal glycosaminoglycan in connective tissue fluids. Commercially available preparations of HA (such as HA Na$^+$ salt) can be used to prepare the macromer. HAs having a molecular weight in the range of $5 \times 10^4$–$2 \times 10^6$, or $1 \times 10^5$–$2 \times 10^6$ Da can be used.

Any sort of water-soluble HA polymer or water-soluble HA polymer derivative can be used as a macromer component in the present invention. Water-soluble esterified derivatives of HA, such as HAs having partial esterification, can be included in the matrix forming composition. For example, derivatives of HA such as benzyl esters of HA (Italiano, G. et al. (1997) Urol. Res., 25(2):137-42) can be used as macromers in the present hydrogel-forming compositions. In other aspects, low molecular weight fragments of HA (Chen and Abatangelo (1999) Wound Repair Regen., 7:79-89) can be used as macromers in the present matrix-forming compositions.

Hyaluronic acid can be obtained from eukaryotic sources such as bovine vitreous humor, rooster combs, or umbilical cords, and also can be obtained from bacterial sources such as Streptococcus zooepidemicus. Depending on the desired use for a polymerizable composition that includes HA, one or more of these sources can be used for the preparation of the composition.

In many aspects, the hydrogel can be formed using polymers, such as macromers or polymers having pendent reactive pairs, at a total concentration of about 50% or greater, which allows for the formation of a hydrogel having at least moderately firm properties and suitable for use within the joint. More desirably the total concentration of macromer is 75% or greater, and concentrations of about 90% or greater have been found to produce a relatively firm gel.

However, in some aspects a lower concentration of polymer may be used. For example, if supporting tissue such as an annulus surrounds the pillow, the hydrogel may have a lower strength and modulus. In these aspects, for example, the total concentration of polymer can be less than 50%.

The hydrogel-forming composition can also include monomers that provide the formed hydrogel with hydrophobic segments. The hydrophobic segments can regulate the amount of water drawn into the hydrogel and provide strength to the hydrogel. U.S. Pub. No. 2006/0093648 describes hydrogels that are useful within joints. Hydrophilic macromers, such as PEG macromers, can be copolymerized with amphiphilic monomers such as diacetone acrylamide (DAA), vinyloxyethanol (VOE), 2-acrylamido-2-methylpropane (AMPS), and methyl acryloyl lactate (ALM) and its relatives.

In another aspect, the hydrogel-forming composition can also include a blend of two or more different macromers. In some aspects, the composition includes a first macromer that is highly hydrophilic and provides significant water retention properties to the hydrogel, and a second macromer that has a low molecular weight and provides the hydrogel with a relatively high modulus. In some aspects the first macromer comprises a plurality of pendent charged groups. For example, the charged groups can be selected from the group of carboxylate, amine, and sulfhydryl groups. The second macromer has a low molecular weight, desirably about 5000 Da or less, or about 2500 Da or less. One exemplary mixture includes a HA macromer and a PEG macromer.

In some aspects the hydrogel-forming composition includes the first (highly hydrophilic) macromer at a concentration of about 1% or greater and a second (low molecular weight) macromer at a concentration of about 40% or greater. An exemplary range for the first macromer is from about 1% to about 10%. An exemplary range for the second macromer is from about 40% to about 80%.

An exemplary composition includes a HA macromer at a concentration of about 10% and a PEG macromer at a concentration of about 50%.

The hydrogel-forming composition can also include one or more other ancillary reagent(s) that help promote formation of the hydrogel following delivery of the composition to the casing. These reagents can include polymerization co-initiators, reducing agents, and/or polymerization accelerants known in the art. These ancillary agents can be included in the composition at any useful concentration.

Exemplary co-initiators include organic peroxides, such as those that are derivatives of hydrogen peroxides ($H_2O_2$) in which one or both of the hydrogen atoms are replaced by an organic group. Organic peroxides contain the —O—O— bond within the molecular structure, and the chemical properties of the peroxides originate from this bond. In some aspects of the invention, the peroxide polymerization co-initiator is a stable organic peroxide, such as an alkyl hydroperoxide. Exemplary alkyl hydroperoxides include t-butyl hydroperoxide, p-diisopropylbenzene peroxide, cumene hydroperoxide, acetyl peroxide, t-amyl hydrogen peroxide, and cumyl hydrogen peroxide.

Other polymerization co-initiators include azo compounds such as 2-azobis(isobutyronitrile), ammonium persulfate, and potassium persulfate.

The hydrogel-forming composition can include a reducing agent such as a tertiary amine. In many cases the reducing agent, such as a tertiary amine, can improve free radical generation. Examples of the amine compound include primary amines such as n-butylamine; secondary amines such as diphenylamine; aliphatic tertiary amines such as triethylamine; and aromatic tertiary amines such as p-dimethylaminobenzoic acid.

In other aspects of the invention, in addition to these components, the composition used to form the hydrogel can include one or more polymerization accelerator(s). A polymerization accelerator such as n-vinyl pyrrolidone can be used. In some aspects a polymerization accelerator having a biocompatible functional group (e.g., a biocompatible polymerization accelerator) is included in the composition of the present invention. The biocompatible polymerization accelerator can also include an N-vinyl group such as N-vinyl amide group. Biocompatible polymerization accelerators are described in commonly assigned U.S. Patent Application Publication No. 2005/0112086.

Formation of the hydrogel in the casing can be initiated by any suitable mechanism. Formation can be initiated prior to, during, of after the in situ delivery of the hydrogel to the casing. In some aspects, the composition includes polymerizable material, such as one or more macromers, and formation of the hydrogel is caused by the combination of an oxidizing agent/reducing agent pair, a "redox pair," in the presence of the polymerizable material.

The oxidizing agent can be selected from inorganic or organic oxidizing agents, including enzymes; the reducing agent can be selected from inorganic or organic reducing agents, including enzymes. Exemplary oxidizing agents include peroxides, including hydrogen peroxide, metal oxides, and oxidases, such as glucose oxidase. Exemplary reducing agents include salts and derivatives of electropositive elemental metals such as Li, Na, Mg, Fe, Zn, Al, and reductases. In one aspect, the reducing agent is present in the composition at a concentration of 2.5 mM or greater when mixed with the oxidizing agent. Other reagents, such as metal or ammonium salts of persulfate, can be present in the composition to promote polymerization of the hydrogel-forming composition.

The redox pair can be combined in the presence of the polymerizable material in any suitable manner. For example, members of the redox pair can be mixed with the polymerizable material prior to delivering the composition to the casing. In another mode of practice, a first composition including the oxidizing agent, and a second composition including the reducing agent (wherein either or both the first or second compositions include the polymerizable material) are independently delivered to the casing and mixed in situ. Upon mixing polymerization commences and the hydrogel begins to form. In yet another mode of practice, the composition includes an oxidizing agent (or reducing agent) and polymerizable material, and the casing includes the reducing agent (or oxidizing agent).

Testing can be carried out to determine mechanical properties of the hydrogel. Dynamic mechanical thermal testing can provide information on the viscoelastic and rheological properties of the hydrogel by measuring its mechanical response as it is deformed under stress. Measurements can include determinations of compressive modulus, and shear modulus. Key viscoeslatic parameters (including compressive modulus and sheer modulus) can be measured in oscillation as a function of stress, strain, frequency, temperature, or time. Commercially available rheometers (for example, available from (TA Instruments, New Castle, Del.) can be used to make these measurements. The testing of hydrogels for mechanical properties is also described in Anseth et al. (1996) *Mechanical properties of hydrogels and their experimental determination*, Biomaterials, 17:1647.

The hydrogel can be measured to determine its complex dynamic modulus (G*): $G^*=G'+iG''=\sigma^*/\gamma^*$, where G' is the real (elastic or storage) modulus, and G" is the imaginary (viscous or loss) modulus, these definitions are applicable to testing in the shear mode, where G refers to the shear modulus, $\sigma$ to the shear stress, and $\gamma$ to the shear strain.

The nucleus pulposus (a hydrogel-like tissue) has a shear modulus G* of about 10 kPa. Hydrogels according to the present invention and having shear moduli at or about this value can be used to replace part or all of the nucleus pulposus.

The hydrogels of the present invention can have a relatively high compressive modulus, such as greater than 100 kPa, or greater than 500 kPa. Some hydrogel-like tissues have compressive moduli of about 1 MPa. Hydrogels described herein, designed to replace or augment their biologic counterparts can be prepared with compressive moduli of 100 kPa or greater, than 500 kPa or greater, or 1 MPa or greater by utilizing compositions that include lower molecular weight macromers at high concentration. If the strength of the casing is great, hydrogels with a lower modulus can be formed, as the casing will support the structure of the hydrogel. Conversely, if the casing is weak, it is desired to have a hydrogel with a greater modulus.

The hydrogel can also be measured for its swelling (or osmotic) pressure. Commercially available texture analyzers (for example, available from Stable Micro Systems; distributed by Texture Technologies Corp; Scarsdale, N.Y.) can be used to make these measurements. Texture analyzers can allow measurement of force and distance in tension or compression.

Some hydrogel-like tissues, such as nucleus pulposus, have swelling pressures of about 300 kPa. Hydrogels according to the present invention and having swelling pressures in the range of 200 kPa-400 kPa can be used to replace part or all of the nucleus pulposus.

Depending on the function of the hydrogel, the ability to swell upon hydration is desirable. Hydrogels described herein can possess swelling ratios from 0.2-10.

The casing and/or the composition that includes the hydrogel-forming material can also include a radiopacifying material. In the insertion process, the radiopacifying material can be included to facilitate the proper positioning of the pillow within the intervertebral disc space. The radiopacifying material can also facilitate monitoring the pillow after insertion. Such monitoring can be used to determine if there is any unwanted movement of the pillow within or out of the intervertebral space. The radiopacifying material can also be used to monitor the integrity of the pillow. Exemplary radiopacifying materials include iodine and platinum-iridium.

The system and method of the present invention can be employed to form a casing-encompassed hydrogel in any orthopedic joint of the body in a minimally invasive manner. However, the method of the present invention is exemplified by a process of forming a synthetic intervertebral disc pillow in a portion of, or all of, the intervertebral disc space.

The process of the present invention can be indicated for patients having a diseased or herniated lumbar disc. Often, degenerated or herniated discs are located between vertebra L4 and L5, or L5 and S1. Herniations are commonly manifested by a fragment of the disc nucleus pushed out of the annulus and into the spinal canal through a tear or rupture. Herniated discs are commonly located in the lumbar spine, and are sometimes found in the cervical spine.

The process can include performing a discectomy, which results in removal of at least a portion of nucleus pulposus. Discectomy is commonly performed to remove degenerated nucleus material. In some cases the discectomy can be performed leaving most or all of the outer annular shell intact. In other cases a portion of the annular shell may be removed. If the annulus is at least partially intact, it may have sufficient strength and integrity to support the pillow within a target location during the process of forming the pillow. Microsurgical techniques, which are also minimally invasive, can be carried out to perform the discectomy.

The minimally invasive process can include performing a laminotomy to gain access to the annulus. An incision in the annulus can be made to gain access to the nucleus area. The incisions that are made to gain access to the intervertebral site can be nominal and do not have to be greater than the maximal cross section of the distal end of the insertion instrument. For example, in order to gain access to the target site, the incisions can be less than about 5 mm, such as in the range of about 2 mm to about 5 mm.

In the insertion process, the casing may be delivered to the intervertebral space when the patient is in a prone position. In this position, the pressure along the spinal column is relieved, and maximum separation between the vertebra can be achieved. In the process, microsurgical techniques can be performed to gain access to the intervertebral space.

The process can also be carried by optionally including a step of distracting the vertebra. A distraction mechanism can be used that promotes the separation of the vertebra adjacent the target intervertebral space. For example, distraction of the disc space can be performed by delivering an inflatable elastomeric balloon or bladder to the intervertebral space. The inflatable balloon or bladder can be delivered to the intervertebral space prior to or at the same time the casing is delivered.

In some aspects the casing is inflated to provide a distraction mechanism. Following delivery to the intervertebral space, air can be delivered to the casing to inflate the casing. The casing can also include a material that temporarily restricts the passage of air through the casing. For example, the casing can include a biodegradable polymer that restricts air passage. Following inflation, and after formation of the hydrogel within the casing, the biodegradable polymer can degrade and allow the movement of fluids. The casing can be impregnated with a natural biodegradable polymer, such as maltodextrin.

In some aspects, the casing is loaded into arthroscopic insertion instrument to facilitate insertion of the casing into a target site within a joint. The insertion instrument is used in a manner to coincide with the minimally invasive procedure. In other words, a portion of the insertion instrument generally has a shape and dimensions that are relatively small and which, in use, do not require extensive disruption of tissue in order to facilitate deliver of the casing to the target site. The insertion instrument can have a distal end that is used to essentially hold the casing in the compact configuration in place during at least the insertion step. For example, the casing in a compact configuration is held within a distal portion of the insertion instrument.

Figure 3:
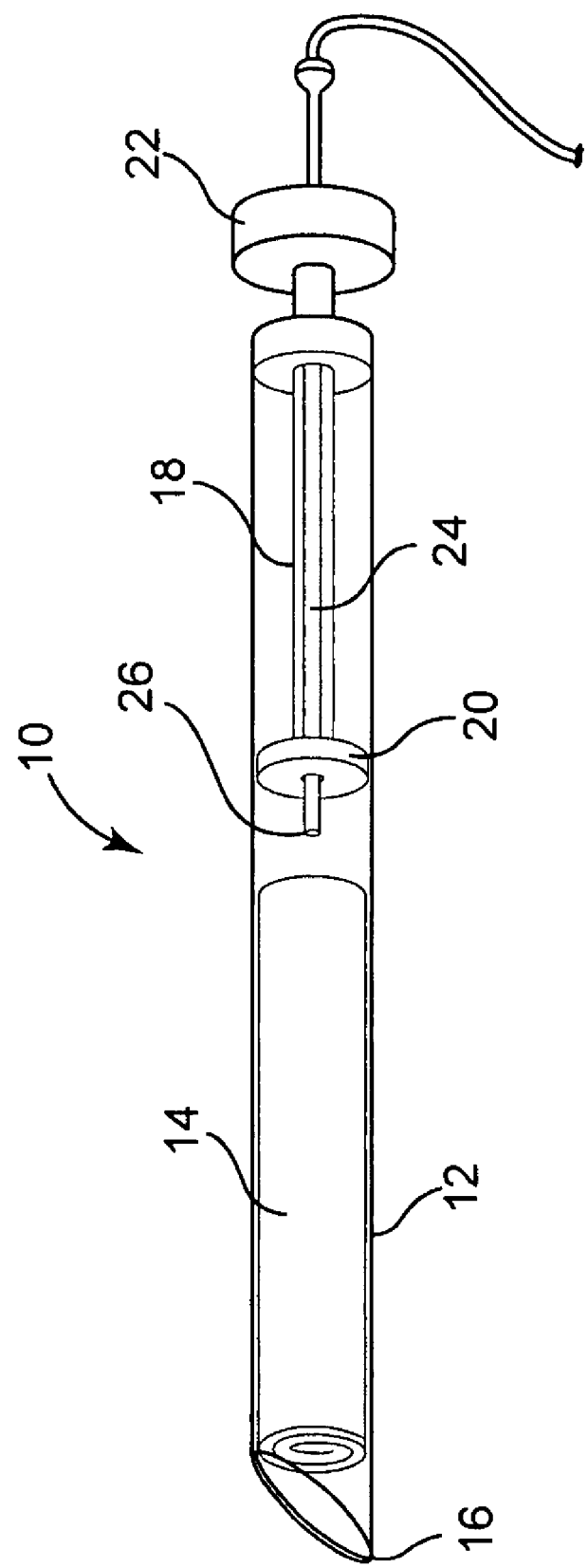
FIG. 3 is a perspective view of one embodiment of an insertion instrument with a casing in a compact configuration loaded in the distal portion of the instrument.

FIG. 3 shows an exemplary insertion instrument 10 with distal portion 12 and a casing 14 loaded in the bore of the distal portion 12. The distal portion 12 of the insertion instrument can have a shape and size suitable to be passed through tissue to the target site within a joint where the casing is deployed. The distal portion 12 can resemble a cannula, but may have any sort of suitable cross sectional shape, such as a circular or non-circular shape. FIG. 3 shows the distal portion of the instrument with a circular cross section and having a beveled distal end 16. The cross section of the distal portion can alternatively have a non-circular cross sectional shape (for example, the cross sectional shape can be oval, rectangular, square, etc). The cross sectional shape of the distal portion can be chosen based on one or more factors, including the anatomy of the target site, the anatomy and type of tissue that the distal end is passed through during the delivery step, the size of the casing, and the configuration of the casing when in the compacted form.

A cross section of the distal end can have a maximal cross sectional dimension. In the case of a circular cross sectional shape, the maximal cross sectional dimension correlates to the outer diameter of the distal portion. In some aspects the maximal cross sectional dimension of the distal end is about 1 cm or less. For example, a circular cross sectional dimension of the distal end is in the range of about 0.25 cm to about 1 cm.

Figure 4:
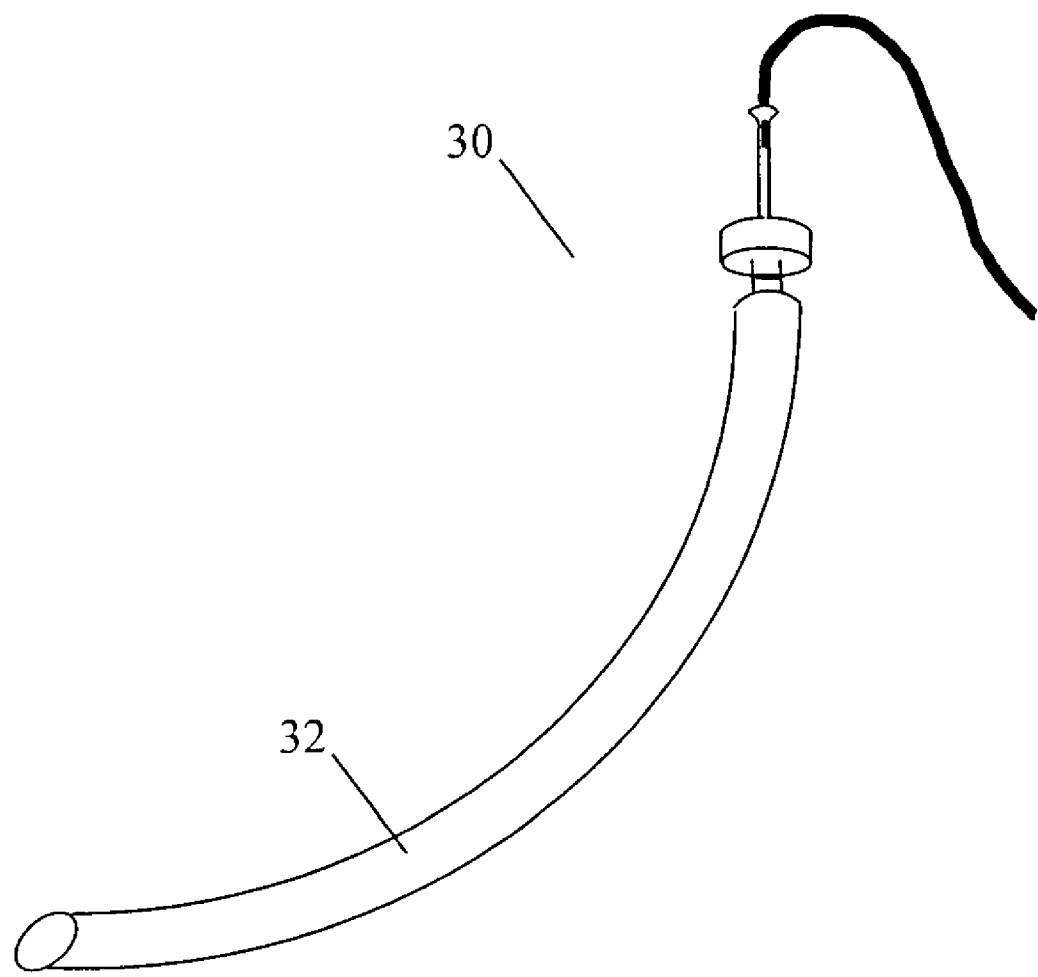
FIG. 4 is a perspective view of another embodiment of an insertion instrument having a curved distal portion.

The insertion instrument shown in FIG. 3 has a linear distal portion. However, non-linear distal portions may also be used. For example, FIG. 4 shows an insertion instrument 30 with a distal portion 32 having a curved shape to facilitate the insertion process. A non-linear shape may allow the insertion process to be performed by avoiding disturbing tissues of an anatomical area, such as the spine.

The distal portion can be fabricated from any suitable material, including plastics, composites, ceramics, metals, and metal alloys. In some cases it can be desirable to use a material that can be readily sterilized, for example, by heat and/or pressure sterilization, such as autoclaving, or by irradiation, such as gamma irradiation, or by chemical sterilization, such as ethylene oxide sterilization.

In some cases, the distal portion of the instrument is substantially or completely inflexible. To achieve this, the distal end can be constructed from a strong or hardened material, such as stainless steel or hardened plastic.

In other cases, the distal portion of the instrument is flexible. A flexible distal portion can be manipulated during the insertion process to properly locate the distal end of the instrument to the target site. Advantageously, the casing that is held within the flexible distal portion is also flexible along with the distal portion. A flexible distal end may provide the user with the ability to navigate the distal end to the treatment site.

The step of delivering the casing to the intervertebral space can be carried out using arthroscopic visualization.

Referring back to FIG. 3, in the step of delivering, the distal end 16 of the instrument can be placed at or within the intervertebral space. In some modes of practice, the distal end can be placed through an opening made in the annulus so that the end is at or within the nucleus region. The casing can then be deployed from the bore of the distal portion 12 by sliding plunger 18, in a distal to proximal direction. The distal end of the plunger can include a stopper 20 that contacts the proximal portion of the casing in the compact configuration. The proximal end of the plunger 18 can include a knob 22 which can be grasped by the user to facilitate the movement of the plunger 18. The casing is forced out of the distal end of the instrument and into the intervertebral space.

The insertion instrument 10 can also include a conduit 24, which is disposed within a bore of the plunger 18 and slidable in relation to the plunger 18. The conduit 24 can be used to deliver the hydrogel-forming composition to the interior of the casing. The conduit 24 can be made of a material suitable for delivery of the hydrogel. For example, the conduit can be made of polyurethane or polyamide tubing. A suitable diameter of the tubing may be about 1 mm although larger or smaller diameters can be used. The proximal end of the conduit 24 is in fluid communication with a receptacle (not shown) that supplies the hydrogel-forming composition.

The distal end 26 of the conduit 24 can be located within the interior of the casing 14 during the step of delivering the casing to the intervertebral site. During the step of delivering, the conduit 24 is moved along with the plunger 18. In another mode of practice, the distal end 26 of the conduit penetrates the casing 14 after the casing has been delivered to the intervertebral space. In this mode, the distal end 26 can be located within or proximal to the stopper 20. After the stopper 20 has forced the casing from the distal portion 12 of the instrument into the intervertebral space, the conduit 24 is slid distally so the distal end 26 penetrates the casing. The distal end 26 can be sharpened to pierce a portion of the casing.

Figure 5:
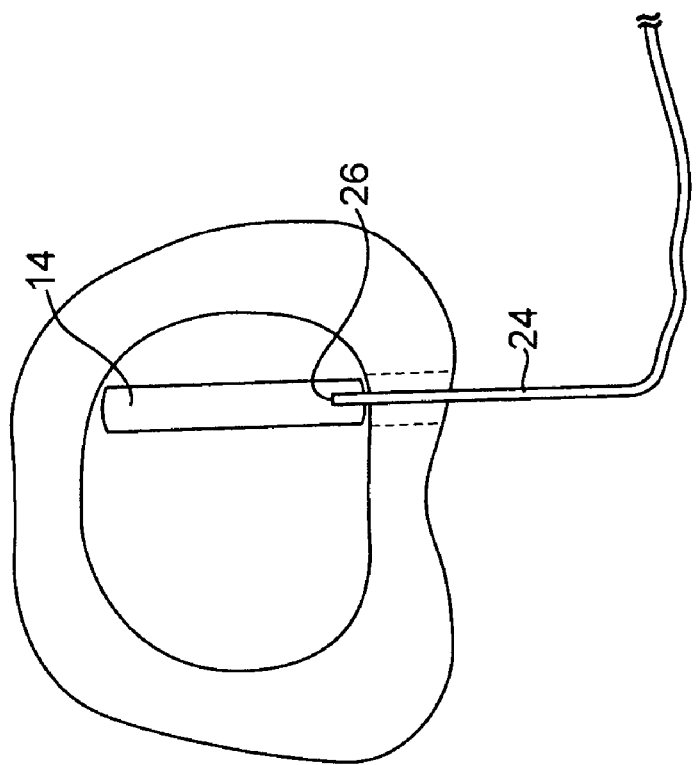
FIG. 5 is an illustration of a denucleated intervertebral disc with a casing in a compact configuration deployed in the denucleated area.

Referring to FIG. 5, with the conduit 24 remaining stationary, the distal portion of the instrument (not shown) can be withdrawn from the intervertebral space, leaving the casing 14 at the target site with the distal end 26 of the conduit 24 attached. The distal end of the conduit is located within the casing. FIG. 5 illustrates the casing 14, still in a compacted configuration, occupying a portion of the intervertebral space normally occupied by the nucleus.

After the casing has been deployed in the intervertebral space it can transition from a compacted to an uncompacted configuration. In this transition, the casing essentially spreads out within the target space. The transition may be characterized by the unfolding, unrolling, or unfurling (or combinations of these events depending on the compacted configuration) of the casing within the target site.

The transition can be facilitated by, for example, the material properties and/or the construction of the casing, or by performing an action that will facilitate the transition. In many cases, the process of delivering the composition via the conduit can be sufficient to cause the transition to the uncompacted configuration. That is, the pressure exerted by the hydrogel forming composition on the inner walls of the casing will be sufficient for it to unfold or unravel. In other cases, the conduit can be used to deliver air to the casing to cause its inflation. If the casing is inflated it may be more easily positioned in the intervertebral space.

Figure 6:
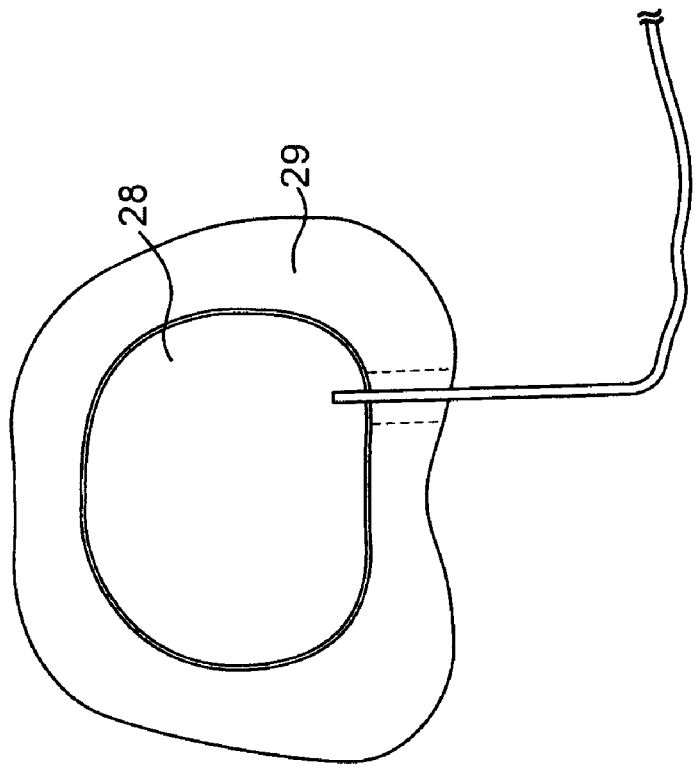
FIG. 6 is an illustration of a denucleated intervertebral disc with a casing in a uncompacted configuration deployed in the denucleated area.

FIG. 6 illustrates the pillow 28 occupying the intervertebral space normally occupied by the nucleus and encompassed by the annulus 29. As seen in this figure, the system and method of the invention is particularly useful for creating an intervertebral pillow that can occupy a substantial portion of the intervertebral space. This can be achieved, however, with minimal tissue disruption.

The hydrogel-forming composition can be delivered to the casing via the conduit. In some modes of practice all of the composition is delivered to the casing after the casing has been deployed from the distal end of the instrument. In other modes of practice, a portion of the composition is delivered before the casing is fully deployed, and the remaining portion is delivered after the casing has been fully deployed. By delivering the composition at different stages in the insertion process, the positioning and transition to the uncompacted state may be enhanced.

The hydrogel forming composition can be delivered to the casing at a rate sufficient to complete the filling in a desired period of time. Generally, it is desired to deliver the composition so that the hydrogel forms as a cohesive hydrogel mass, rather than a plurality of disparate hydrogel fragments. The rate of delivery of the composition can be increased by utilizing a larger conduit or multiple conduits, or by using a low viscosity composition, or combinations of these. In some modes of practice the composition is delivered to the casing at a rate of about 500 uL/sec.

The composition is generally delivered in an amount sufficient to fill the casing. The amount delivered will depend on the geometry of the casing, which can be dictated by the joint. In some aspects, the amount of hydrogel delivered is greater than about 0.75 mL, and in some aspects between about 0.75 mL and about 5 mL.

Commencement of hydrogel formation can occur before, during, and/or after the composition is delivered to the casing. In some aspects the composition includes macromers, and a polymerization initiator system is activated prior to delivering the composition to the casing via the conduit. For example, in some modes of practice, a first macromer composition including an oxidizing agent, and a second macromer composition including a reducing agent are combined, mixed, and then injected into the conduit. One type of suitable mixing device comprises injection ports and a chamber having a series of baffles in which the compositions are mixed (Mixpac™; commercially available from Mixpac™ Systems AG, Rotkreuz, CH). Mixing of the composition occurs immediately prior to introduction of the mixed compositions into the conduit and does not clog the conduit.

Optionally, the instrument can include a second conduit that can have a distal end that is also attached to the casing.

The pillow in its final form, that is, the casing having the cured hydrogel, can have a desired shape within the joint. In some cases, the shape of the pillow will conform to a particular area within the joint. For example, in an intervertebral joint that is denucleated but having most or all of the annulus intact, the shape of the pillow can at least substantially conform to the shape of the denucleated area. The ability to conform to a particular area can be accomplished by a combination of a stretchable casing and the hydrogel composition. Given this, the pillow in the final form may have a shape that is asymmetrical. An asymmetrical shape can be useful for securing the pillow at the desired location within the intervertebral space.

The method and system of the present invention can also provide an orthopedic joint pillow that is not expulsed from the joint. Since a minimally invasive procedure is used to form the pillow within the joint, only a minimal amount of tissue is disrupted during the insertion process. This maintains the integrity of the most of the tissue surrounding the joint, which can provide better retention of the pillow in use.

The invention will be further described with reference to the following non-limiting Examples.

EXAMPLE 1

Synthesis of Acrylated Hyaluronic Acid (HA-Acrylate)

Two grams hyaluronic acid (Lifecore Biomedical, Chaska, Minn.) were dissolved in 100 ml of dry formamide. To this solution were added 1.0 g (9.9 mmol) of TEA and 4.0 g (31 mmol) of glycidyl acrylate. The reaction mixture was stirred at 37° C. for 72 hours. After exhaustive dialysis against deionized water using 12-14 k MWCO dialysis tubing, the product (2.89 grams) was isolated by lyophilization.

EXAMPLE 2

Preparation of Trimethylolpropane Ethoxylate (20/3 EO/OH) Triacrylate (PEG-Triacrylate)

The polyethyleneglycol-triol (PEG-triol; 100.0 g, 98.6 mmoles, Aldrich Chemical Company, Inc., Milwaukee, Wis.) was dissolved with stirring in toluene (200 mLs) and refluxed for one hour. The PEG-triol solution was allowed to cool to approximately 80° C. At this time 4-methoxyphenol (MEHQ; 50 mg, 0.403 mmoles, J. T. Baker, Phillipsburg, N.J.), acrylic acid (42.7 g, 0.592 moles, J. T. Baker, Phillipsburg, N.J.), and sulfuric acid (10 mLs, 0.188 moles, Aldrich Chemical Company, Inc., Milwaukee, Wis.) were added with stirring to the reaction solution. The reaction solution was heated to reflux. The reaction was allowed to progress until about 6.0 mLs of water was produced and collected via a Dean & Stark receiver for approximately one hour. The reaction mixture was allowed to cool to 50° C. and poured into a solution of sodium bicarbonate (270 g in 2.5 liters of deionized water) with stirring. The organic layer was separated, washed with deionized water and dried over sodium sulfate. The PEG-triacrylate was isolated using a wiped film still (Pope Scientific, Inc., Saukville, Wis.).

The structure of the reaction components PEG-triol (a), acrylic acid (b), and the PEG-triacrylate macromer product (c) are shown in the following reaction scheme:

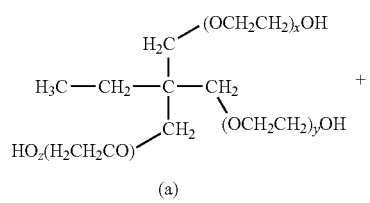

(a)

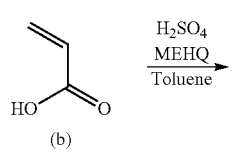

(b)

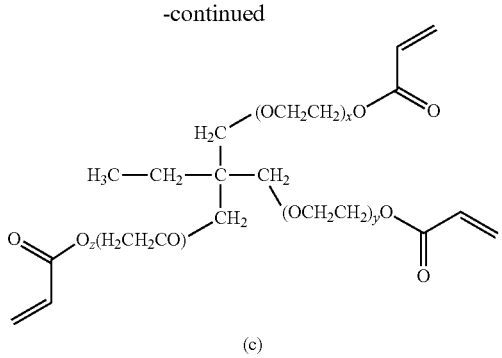

(c)

EXAMPLE 3

Formation of a HA-Acrylate/PEG-Triacrylate Hydrogel Using REDOX Chemistry

Two solutions were prepared. Solution #1 was prepared as follows: 100 mg of HA-acrylate as prepared in Example 1 was placed in an 8 mL vial. To the MD-acrylate was added 15 mg ferrous ascorbate (Sigma), 500 µL PEG-triacrylate (prepared as described in Example 2) and 500 µL deionized water. Solution #2 was prepared as follows: 100 mg of HA-acrylate (Example 1) was placed in a second 8 mL vial. To this HA-acrylate was added 80 µL hydrogen peroxide (Sigma), 500 µL PEG-triacrylate, and 500 uL 0.1 M acetate buffer (pH 5.5).

50 uL of Solution #1 was added to a glass slide. 50 µL of solution #2 was added to Solution #1 with slight mixing. After mixing for 2 seconds, the mixture polymerized and formed a semi-firm gel having elastomeric properties.

EXAMPLE 4

Formation of a HA-Acrylate/PEG-Triacrylate Hydrogel Using REDOX Chemistry

Two solutions were prepared. Solution #1 was prepared as follows: 100 mg of HA-acrylate as prepared in Example 1 was placed in an 8 mL vial. To the HA-acrylate was added 15 mg ferrous ascorbate (Sigma), 100 µL PEG-triacrylate (Example 2) and 900 µL deionized water. Solution #2 was prepared as follows: 100 mg of HA-acrylate as prepared in example 1 was placed in a second 8 mL vial. To this HA-acrylate was added 80 uL hydrogen peroxide (Sigma), 100 µL MR01 and 900 µL 0.1 M Acetate buffer (pH 5.5).

50 µL of Solution #1 was added to a glass slide. 50 µL of solution #2 was added to Solution #1 with slight mixing. After mixing for 2 seconds, the mixture polymerized and formed a semi-firm gel having elastomeric properties.

EXAMPLE 5

Formation of PEG-Triacrylate Hydrogels

Two different UV cured PEG-triacrylate-based hydrogels were prepared, one being moderately firm and the other being firm. The moderately firm hydrogel was prepared from a composition having PEG-triacrylate at a concentration of 50% and the photoinitiator 4,5-bis(4-benzoylphenylmethyleneoxy)benzene-1,3-disulfonic acid disodium salt (prepared as described in U.S. Pat. No. 6,278,018) "DBDS" at 10-mg/mL in 50% water. The firm hydrogel was prepared from a composition having PEG-triacrylate at a concentration of 90% and the photoinitiator DBDS at 2 mg/mL in 10% water.

Each solution above was prepared and sonicated to de-gas. The de-gassed solution was pipetted into a 3.5 cm length of silicone tubing with a diameter of ~4 mm. One end of the tube was sealed and the tube/solution was sonicated to de-gas once more. The tube/solution was then placed in the "Goliath" UV light chamber and illuminated for 60-seconds (with rotation). The cured set-up matrix was then pushed out of the silicone tube. The formed rods were clear and exhibited relatively good toughness. Each rod was squeezed and bent (~20-30 degrees) and there was a distinct difference in firmness and flexibility between the 2 formulations.

Two different redox cured PEG-triacrylate-based hydrogels were prepared, one being moderately firm and the other being firm. The moderately firm hydrogel was prepared from first and second compositions having PEG-triacrylate at a concentration of 43%, and the redox member (either KPS in the first composition or Iron Ascorbate in the second composition) at a concentration of 5.7 mg/mL in 57% water. The moderately firm hydrogel was prepared from first and second compositions having PEG-triacrylate at a concentration of 87%, and the redox member (either KPS in the first composition or Iron Ascorbate in the second composition) at a concentration of 5.0 mg/mL in 13% water.

The above solutions were prepared and sonicated to degas. A static mixer system from "Mixpac" was used (dual syringe; one barrel filled with the KPS solution, the other with the Iron Ascorbate solution) to inject and mix the two solutions simultaneously into a "fabric pillow." The fabric pillow was constructed out of a polypropylene woven cleanroom wipe fabric (2-sheets of the fabric heat sealed together in a square, with a small port-like hole cut to insert the tip of the mixer head). The solutions and Mixpac system were refrigerated to cool down the solutions (to slow the resulting REDOX reaction) for 10 minutes. The solutions were then injected into the fabric pillows. The composition using a higher concentration of macromer (87% PEG) cured to a hydrogel within 2-4 seconds. The composition using a higher concentration of macromer (43% PEG) cured to a hydrogel within 4-6 seconds. The lower concentration matrix was less firm than the high concentration matrix and had some rubber-like qualities.

EXAMPLE 6

Synthesis of Aminated Polyalditol

Vacuum oven-dried Polyalditol PD60 (10.00 g)[Grain Processing Corporation, Muscatine Iowa] was dissolved with anhydrous dimethyl sulfoxide, DMSO, (50 mL) in a 120 mL amber vial. In a separate 30 mL amber vial, 1,1'-carbonyldiimidazole, CDI, (3.00 g) was dissolved in dry DMSO (25 mL). The CDI solution was poured into the maltodextrin solution and purged with nitrogen gas before being capped. The reaction solution was placed on a rotary shaker for 20 minutes. Into a separate 120 mL amber vial, 1,6-diaminohexane (10.80 g) was warmed to 45° C. and dissolved in dry DMSO (10 mL) and a Teflon stir bar was inserted and placed on a stir plate. The polyalditol/CDI solution was slowly poured into the stirred diamine solution after 20 minutes. Once the addition was complete the reaction vial was transferred into a 55° C. oven and allowed to stir overnight. The next day, the reaction solution was precipitated into 1 liter tetrahydrofuran, THF, and a white precipitate formed. The mixture was stirred for one hour and the solvent was decanted. Fresh THF (1 L) was poured into the 2-L Erlenmeyer beaker and the white precipitate was stirred for one hour. This step was repeated twice. The final mixture was filtered using a water-aspirator, Büchner funnel, and Whatman-brand paper filter and a white precipitate was collected (13.14 g). The precipitate was then dried overnight at 40° C. under vacuum. A small sample of the material (50 mg) was dissolved with 5 mL deionized water in a 7-mL vial. To this sample was added 1 mL of ninhydrin solution (3.6 mg/mL in IPA). The sample was capped and heated to 70° C. in a water bath for a couple minutes, after which time the solution turned a dark purple color indicating the presence of primary amines.

EXAMPLE 7

Poly(ethylene glycol)$_{3350}$-di(imidazolyl carbamate)

Vacuum oven-dried poly(ethylene glycol), MW ~3350, (6.70 g) was dissolved with anhydrous tetrahydrofuran, THF, (20 mL) in a 60 mL amber vial with slight heating (40° C.). In another 60 mL amber vial 1,1'-carbonyldiimidazole, CDI, (0.811 g) was dissolved with 10 mL dry THF. A Teflon stir bar was inserted into the CDI solution and placed on a stir plate. The PEG solution was pipetted into the CDI solution while stirring at room temperature. The reaction vial was purged with nitrogen gas once the addition was complete. The reaction was allowed to stir at room temperature for two hours. After two hours, the reaction solution was precipitated into 1 liter of chilled, anhydrous diethyl ether while stirring. The ether solution was decanted, and the precipitate was rinsed three more times (3×1 L) with fresh, anhydrous ether while stirring. The precipitate was collected by vacuum filtration using a water-aspirator, Büchner funnel, and a Whatman-type paper filter. The collected white precipitate (6.84 g) was dried overnight in a vacuum oven (30° C.).

EXAMPLE 8

Poly(ethylene glycol)$_{2000}$-di(imidazolyl carbamate)

Vacuum oven-dried poly(ethylene glycol), MW 2000, (20.00 g) was dissolved with anhydrous tetrahydrofuran, THF, (200 mL) in a 500 mL amber vial with slight heating (40° C.). In another 500 mL amber vial 1,1'-carbonyldiimidazole, CDI, (4.10 g) was dissolved with 50 mL dry THF. A Teflon stir bar was inserted into the CDI solution and placed on a stir plate. The PEG solution was pipetted into the CDI solution while stirring at room temperature. The reaction vial was purged with nitrogen gas once the addition was complete. The reaction was allowed to stir at room temperature for two hours. After two hours, the reaction solution was precipitated into 2 liters of chilled, anhydrous diethyl ether while stirring. The ether solution was decanted and the precipitate rinsed three more times (3×1 L) with fresh, anhydrous ether while stirring. The precipitate was collected by vacuum filtration using a water-aspirator, Büchner funnel, and a Whatman-type paper filter. The collected white precipitate (19.41 g) was dried overnight in a vacuum oven (30° C.).

EXAMPLE 9

Poly(ethylene glycol)$_{1500}$-di(imidazolyl carbamate)

Vacuum oven-dried poly(ethylene glycol), MW 1500, (15.00 g) was dissolved with anhydrous tetrahydrofuran, THF, (150 mL) in a 500 mL amber vial with slight heating (40° C.). In another 500 mL amber vial 1,1'-carbonyldiimidazole, CDI, (4.10 g) was dissolved with 50 mL dry THF. A Teflon stir bar was inserted into the CDI solution and placed on a stir plate. The PEG solution was pipetted into the CDI solution while stirring at room temperature. The reaction vial was purged with nitrogen gas once the addition was complete and the reaction was allowed to stir at room temperature for two hours. After two hours, the reaction solution was precipitated into 2 liters of chilled, anhydrous diethyl ether while stirring. The ether solution was decanted and the precipitate rinsed three more times (3×1 L) with fresh, anhydrous ether while stirring. The precipitate was collected by vacuum filtration using a water-aspirator, Büchner funnel, and a Whatman-type paper filter. The collected white precipitate (14.68 g) was dried overnight in a vacuum oven (30° C.).

EXAMPLE 10

Poly(ethylene glycol)$_{1000}$-di(imidazolyl carbamate)

Poly(ethylene glycol), MW 1000, (20.59 g) was dissolved with anhydrous tetrahydrofuran, THF, (200 mL) in a 500 mL amber vial. In a 500 mL amber vial 1,1'-carbonyldiimidazole, CDI, (8.40 g) was dissolved with 50 mL dry THF. A Teflon stir bar was inserted into the CDI solution and placed on a stir plate. The PEG solution was pipetted into the CDI solution while stirring at room temperature. The reaction vial was purged with nitrogen gas once the addition was complete. The reaction was allowed to stir at room temperature for two hours. After two hours, the reaction solution was precipitated into 2 liters of chilled, anhydrous diethyl ether while stirring. The ether solution was decanted and the precipitate was rinsed three more times (3×1 L) with fresh, anhydrous ether while stirring. The precipitate was collected by vacuum filtration using a water-aspirator, Büchner funnel, and a Whatman-type paper filter. The waxy precipitate (17.59 g) was dried overnight in a vacuum oven (22° C.).

EXAMPLE 11

Poly(ethylene glycol)$_{600}$-di(imidazolyl carbamate)

Poly(ethylene glycol), MW 600, (30.15 g) was transferred to a 150 mL round bottom flask and dissolved with 50 mL dichloromethane (DCM). The solvent was stripped off using a rotary evaporator and high temperature water bath. This step was repeated twice more. In a 500 mL round bottom flask 1,1'-carbonyldiimidazole, CDI, (22.90 g) was dissolved with 250 mL DCM. A Teflon stir bar was inserted into the CDI solution and placed on a stir plate under nitrogen. The PEG$_{600}$ was dissolved with 50 mL DCM and slowly added to the stirring CDI solution and stirred at room temperature for two hours under nitrogen. The reaction solution was transferred into a 1 L separatory funnel and washed twice with 1 mM HCl followed by two brine solution washes. The organic solution was collected and dried with magnesium sulfate. The dried solution was filtered through a Whatman paper filter into a clean 500 mL round bottom flask and the DCM was rotary evaporated with mild heat (30° C.). A clear, slightly yellowish-tinted oil was collected (37.02 g).

EXAMPLE 12

Tetraethylene glycol-di(imidazolyl carbamate)

Tetraethylene glycol, TEG, MW 194.23, (21.80 g) was transferred to a 500 mL round bottom flask and dissolved with dichloromethane, DCM, (100 mL). The solvent was stripped off using a rotary evaporator and high temperature water bath. The stripping step was repeated twice. In a 1000 mL round bottom flask 1,1'-carbonyldiimidazole, CDI, (40.05 g) was dissolved with 380 mL DCM. A Teflon stir bar was inserted into the CDI solution and placed on a stir plate under nitrogen. The TEG was dissolved with 200 mL DCM and was slowly added to the stirred CDI solution, and the mixture was stirred at room temperature for two hours under nitrogen. The reaction solution was transferred into a 1 L separatory funnel and washed twice with 1 mM HCl followed by two brine solution washes. The organic solution was collected and dried with magnesium sulfate. The dried solution was filtered through a Whatman paper filter into a clean 500 mL round bottom flask and the DCM was rotary evaporated with mild heat (30° C.). A clear oil was collected (39.46 g).

EXAMPLE 13

Triethylene glycol-di(imidazolyl carbamate)

Triethylene glycol, TrEG, MW 150.17, (3.01 g) was transferred to a 50 mL round bottom flask and dissolved with dichloromethane, DCM, (30 mL). The solvent was stripped off using a rotary evaporator and high temperature water bath. The stripping step was repeated twice. In a 250 mL round bottom flask, 1,1'-carbonyldiimidazole, CDI, (7.14 g) was dissolved with 100 mL DCM. A Teflon stir bar was inserted into the CDI solution and placed on a stir plate under nitrogen. The TrEG was dissolved with 50 mL DCM and slowly added to the stirred CDI solution, and the mixture was then stirred at room temperature for two hours under nitrogen. The reaction solution was transferred into a 250 mL separatory funnel and washed twice with 1 mM HCl followed by two brine solution washes. The organic solution was collected and dried with magnesium sulfate. The dried solution was filtered through a Whatman paper filter into a clean 250 mL round bottom flask and the DCM was rotary evaporated with mild heat (30° C.). A clear oil was collected (5.93 g).

EXAMPLE 14

Trimethylolpropane ethoxylate (20 EO)-tri(imidazolyl carbamate)

Trimethylolpropane ethoxylate (20/3 EO/OH), MW 1014, (10.14 g) was transferred to a 150 mL round bottom flask and dissolved with dichloromethane, DCM, (50 mL). The solvent was stripped off using a rotary evaporator and high temperature water bath. The stripping step was repeated twice. In a 1000 mL round bottom flask 1,1'-carbonyldiimidazole, CDI, (6.49 g) was dissolved with 250 mL DCM. A Teflon stir bar was inserted into the CDI solution and placed on a stir plate under nitrogen. The trimethylolpropane ethoxylate was dissolved with 100 mL DCM and slowly added to the stirred CDI solution, and the mixture was stirred at room temperature for two hours under nitrogen. The reaction solution was transferred into a 500 mL separatory funnel and washed twice with 1 mM HCl followed by two brine solution washes. The organic solution was collected and dried with magnesium sulfate. The dried solution was filtered through a Whatman paper filter into a clean 500 mL round bottom flask and the DCM was roto evaporated with mild heat (30° C.). A clear oil was collected (12.07 g).

EXAMPLE 15

Pentaerythritol ethoxylate (15 EO)-tetra(imidazolyl carbamate)

Pentaerythritol ethoxylate (15/4 EO/OH), MW 797, (11.96 g) was transferred to a 500 mL round bottom flask and dissolved with dichloromethane, DCM, (100 mL). The solvent was stripped off using a rotary evaporator and high temperature water bath. The stripping step was repeated twice. In a 1000 mL round bottom flask 1,1'-carbonyldiimidazole, CDI, (16.22 g) was dissolved with 200 mL DCM. A Teflon stir bar was inserted into the CDI solution and placed on a stir plate under nitrogen. The pentaerythritol ethoxylate was dissolved with 100 mL DCM and slowly added to the stirred CDI solution, and the mixture was stirred at room temperature for two hours under nitrogen. The reaction solution was transferred into a 500 mL separatory funnel and washed twice with 1 mM HCl followed by two brine solution washes. The organic solution was collected and dried with magnesium sulfate. The dried solution was filtered through a Whatman paper filter into a clean 500 mL round bottom flask and the DCM was roto evaporated with mild heat (30° C.). A clear oil was collected (15.89 g).

EXAMPLE 16

Preparation of Hydrogels from Aminated Polyalditol and Di(Imidazolyl Carbamate)-Modified Alkoxyalkane Polymers Hydrogel A A hydrogel matrix was formed according to the following process. Solution A was prepared by dissolving 213 mg of aminated-PD60 (Example 6) with 0.5 mL of PBS solution (pH ~7.5) into a 8-mL glass vial. The pH of solution A was lowered to ~7.5 using concentrated HCl (14 uL). The final concentration aminated-PD60 in the solution A was approximately 414 mg/mL.

Solution B was prepared prior to use by pipetting 150 uL of neat triethylene glycol diimidazoyl carbamate (TrEG-diIC) into a 1-mL clear HPLC vial with screw cap. The neat TrEG-diIC was diluted with 50 uL of diH$_2$O to make a 75:25 (v/v) solution.

Matrix formation was accomplished by injecting 100 uL of solution A (conc. ~400 mg/mL & pH ~8.5) into a 1-mL clear HPLC vial followed by injection of 13.4 uL of Solution B. The vial was capped and vortexed for 30 seconds to mix. The solution viscosity increased slowly until the material reached its gel point, which is defined as the materials resistance to flow upon inversion of the sample. The time required to reach the gel point was observed to be eight minutes. The hydrogel matrix was clear with a slight yellowish tint. The matrix was soft and fragile; however it demonstrated limited swelling upon addition of 0.5 mL diH$_2$O.

Hydrogel B

A hydrogel matrix according to the process used to form hydrogel A, but using double the volumes of solutions A and B (200 uL PD60-amine & 26.8 uL TrEG-diIC). The observed gel time increased to ten minutes. The hydrogel matrix was clear with a slight, yellowish tint. The hydrogel was soft and fragile, yet demonstrated limited swelling upon addition of 0.5 mL diH2O after ten minutes.

Hydrogel C

A hydrogel matrix was formed according to the process used to form hydrogel A, but using PD60-amine (Example 6) combined with PEG$_{600}$-diIC (Example 11) at a 2:1 ratio.

Hydrogel D

A hydrogel matrix was formed according to the process used to form hydrogel A, but using PD60-amine (Example 6) combined with PEG$_{600}$-diIC (Example 11) at a 1:1 ratio.

Hydrogel E

A hydrogel matrix was formed according to the process used to form hydrogel A, but using PD60-amine (Example 6) combined with PEG$_{3500}$ diIC (Example 7) at a 1:1 ratio.

EXAMPLE 17

Hydrogel Testing

Hydrogels C, D, and E formed in Example 16 were subjected to rheological testing to determine storage modulus (G', Pa) and phase angle using an AR Rheometer (TA Instruments, New Castle, Del.). Time sweep tests were performed at 1% strain and 1 rad/sec oscillation. Also a frequency sweep (0.1-100 rad/sec @ 1% strain) was done on the hydrogels to determine if the phase angle increased with higher frequency.

Figure 7:
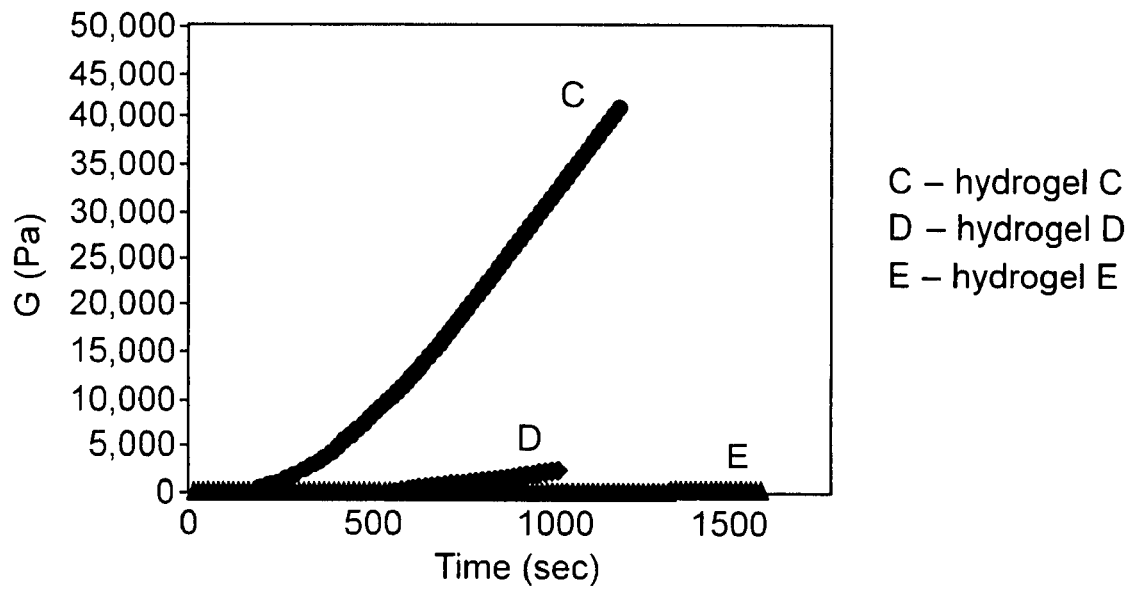
FIG. 7 is a graph showing the change in storage modulus over time for three different hydrogels.
Figure 8:
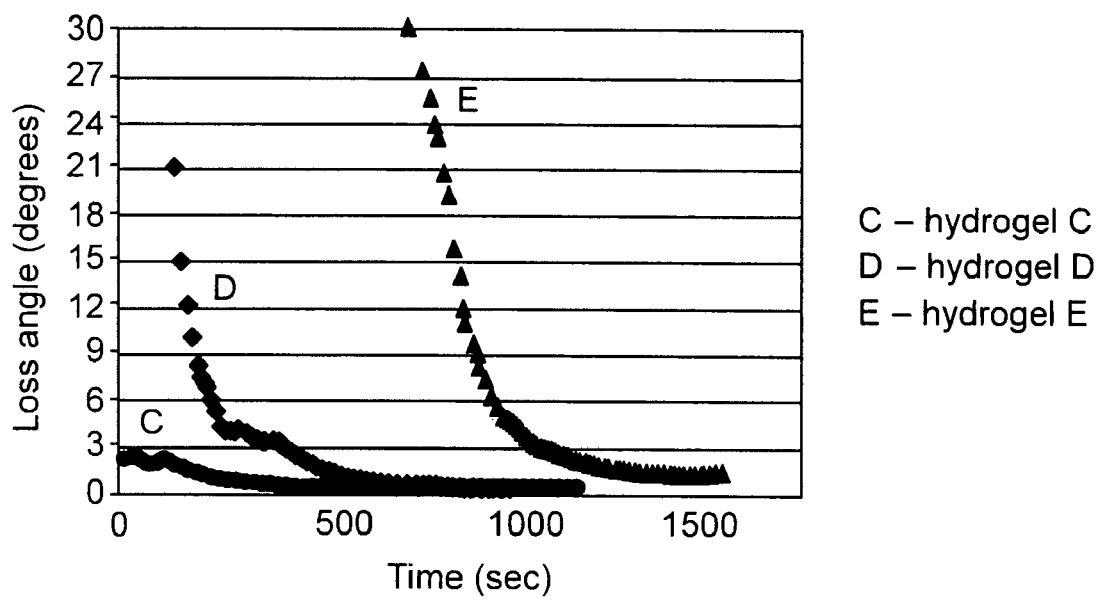
FIG. 8 is a graph showing the change in phase angle over time for three different hydrogels.
Figure 9:
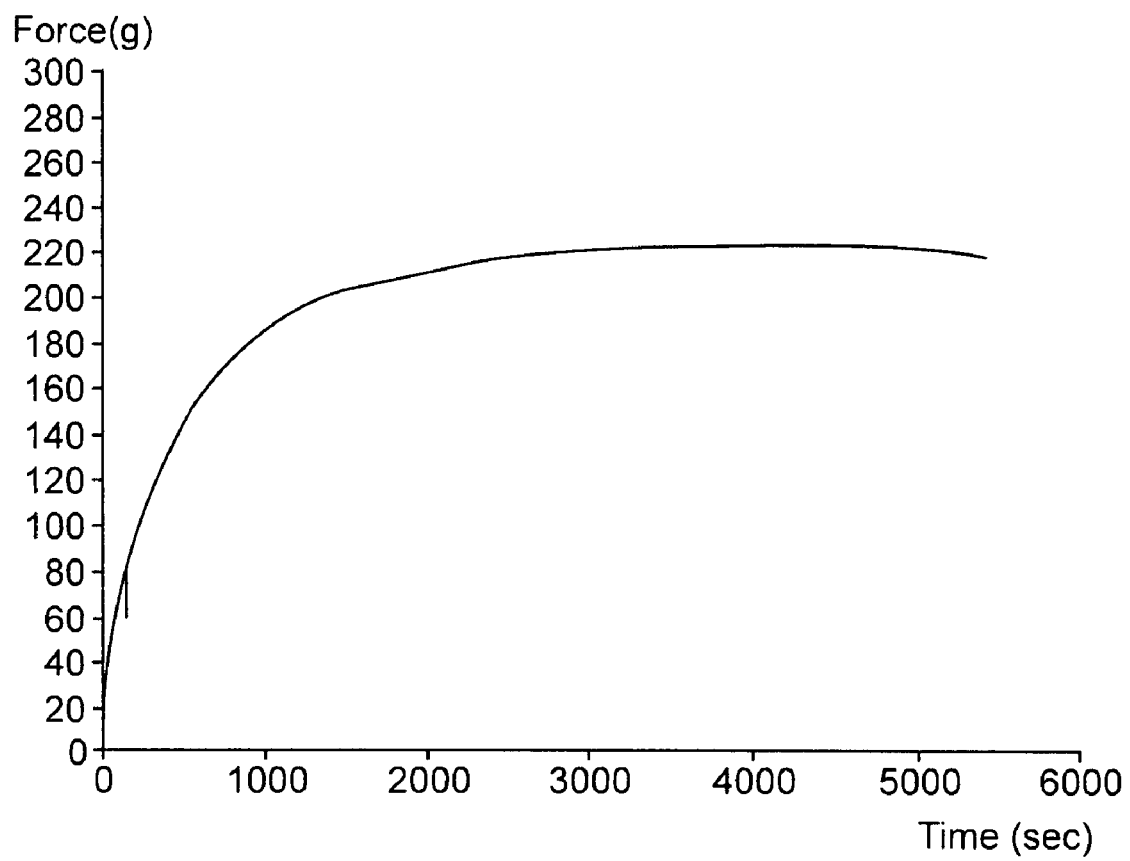
FIG. 9 is a graph showing the change in swelling pressure of a hydrogel pellet over a period of time in which the pellet was rehydrated.

Results of the rheological testing for storage modulus and phase angle are shown in FIGS. 7-8. Time sweep tests gave different results for the three hydrogels. The stiffest sample (hydrogel C) had a shear modulus of about 20–30 kPa, but a loss angle of less than 1 degree. Hydrogels C and E had shear moduli of less than 2 kPa and a loss angle of less than 2°. A frequency sweep on hydrogel E showed that there is some increase in the loss angle at higher frequencies, reaching about 20° at 100 rad/sec.

A TA.XTPlus Texture Analyser (Stable Micro Systems; distributed by Texture Technologies Corp; Scarsdale, N.Y.), which is an instrument used in compressive and tensile testing applications, was used to perform rheological testing. Texture analyzer testing, using a compressive test method developed with in the TA.XTPlus software, was performed to determine swelling pressure and comprehensive modulus. Formulations that showed the greatest amount of swelling were formulated and dried down to pellets in molds. The dimensions and weights of the dried pellets were taken before the testing. The pellets were then loaded into a well and compressed into place, with a flat bottom probe. A static trigger force of 4 g, was placed onto the pellet, and this provided the initial force on the pellet. Then the pellet was hydrated with DI water to determine the swelling and compression pressure, and swelling ratio. With the dimensions of the pellet loaded into the TA.XTPlus software, a macro was created to take the measurements of swelling pressure.

The initial hydration of the pellet from hydrogel E took about 40 minutes and created a swelling pressure of about 220 grams force (about 68 kPa) of pressure (based on a ¼ inch surface area; P=F/A). After the initial swelling pressure was measured, the pellet remained in the DI water to fully hydrate.

What is claimed is:

1. A hydrogel forming composition for the treatment of an orthopedic condition, the composition comprising a trimethylolpropane ethoxylate triacrylate first polymer having a molecular weight of less than 5000 Da, and second polymer that is water soluble at pH 7.5, wherein the first and second polymer comprise reactive groups which are reacted to form a hydrogel to treat the orthopedic condition.

2. The hydrogel forming composition of claim 1 wherein the second polymer is derived from a polymer selected from heparin, hyaluronic acid, maltodextrin, amylose, and polyalditol.

3. The hydrogel forming composition of claim 1 wherein the second polymer comprises a polysaccharide having pendent amine groups.

4. The hydrogel forming composition of claim 1, wherein the first and second polymers comprise pendent free radical polymerizable groups and the composition further comprises a free radical polymerization initiator.

5. The hydrogel forming composition of claim 4, wherein the second polymer comprises acrylated hyaluronic acid.

6. The hydrogel forming composition of claim 1, wherein the first polymer has a molecular weight in the range from about 200 Da to about 3500 Da.

7. The hydrogel forming composition of claim 1, wherein the first and second polymers comprise pendent first and second reactive groups, that are amine-reactive groups, and amine groups.

8. The hydrogel forming composition of claim 7, wherein the second polymer comprises aminated polyalditol.

9. The hydrogel forming composition of claim 7, having a stoichiometric ratio of amine groups to amine-reactive groups in the range of 1:5 to 5:1, respectively.

10. The hydrogel forming composition of claim 1, wherein the second polymer comprises a polysaccharide and degree of substitution with the reactive group in the range of 0.1 to 1.0.

11. The hydrogel forming composition of claim 1, having a pH in the range of about 7.5 to about 9.5.

12. The hydrogel forming composition of claim 1, where, in the composition, the first polymer is present at a concentration of 1% wt or greater, and the second polymer is present at a concentration of 40% wt or greater.

13. The hydrogel forming composition of claim 12, where, in the composition, the first polymer is present at a concentration in the range of 1-10% wt, and the second polymer is present at a concentration of 40-80% wt.

14. The hydrogel forming composition of claim 1, configured to provide a hydrogel having a compressive moduli of 100 kPa or greater.

* * * * *